United States Patent
Atkins et al.

(10) Patent No.: US 7,355,035 B1
(45) Date of Patent: Apr. 8, 2008

(54) CATALYTIC MOLECULES

(75) Inventors: David G. Atkins, New York, NY (US); Andrew R. Baker, Wahroonga (AU); Levon Michael Khachigian, Ryde (AU)

(73) Assignee: Unisearch Limited, Sydney (AU)

( * ) Notice: Subject to any disclaimer, the term of this patent is extended or adjusted under 35 U.S.C. 154(b) by 0 days.

(21) Appl. No.: 09/889,075

(22) PCT Filed: Jan. 11, 2000

(86) PCT No.: PCT/AU00/00011

§ 371 (c)(1),
(2), (4) Date: Sep. 9, 2002

(87) PCT Pub. No.: WO00/42173

PCT Pub. Date: Jul. 20, 2000

(30) Foreign Application Priority Data

Jan. 11, 1999 (AU) .................................. PP8103

(51) Int. Cl.
C07H 21/04 (2006.01)
C07H 21/02 (2006.01)
A61K 48/00 (2006.01)
C12Q 1/68 (2006.01)

(52) U.S. Cl. .................. 536/24.5; 435/6; 435/325; 435/375; 514/44; 536/23.1; 536/24.3

(58) Field of Classification Search .................. 514/44; 435/6, 325, 375; 536/23.1, 24.5
See application file for complete search history.

(56) References Cited

FOREIGN PATENT DOCUMENTS

| WO | WO 96/17086 | 6/1996 |
|---|---|---|
| WO | WO 97/32979 | 9/1997 |
| WO | WO 98/49346 | 11/1998 |
| WO | WO 99/50452 | 10/1999 |

OTHER PUBLICATIONS

Jen et al. (Stem Cells 2000, vol. 18, p. 307-319.*
Opalinska et al. (Nature Reviews Drug Discovery, 2002, vol. 1, p. 503-514.*
Braasch, D. A. Biochemistry. Apr. 2002; 41(14): 4503-4510.*
Branch, A. D.,Trends Biochem Sci. Feb. 1998;23(2):45-50.*
Tamm, I. et al. The Lancet. Aug. 2001, 358: 489-497.*
Cairns et al., "Target Site Selection for an RNA-Cleaving Catalytic DNA" *Nature Biotechnology*, vol. 17, pp. 480-486, May 1999.
Milbrandt, J. Rat nerve growth factor-induced (NGFI-A) gene complete cds. 1987. Genbank Accession No. M18416.
Santiago et al., "New DNA Enzyme Targeting Egr-1 mRNA Inhibits Vascular Smooth Muscle Proliferation and Regrowth After Injury" *Nature Medicine*; vol. 5, No. 11, pp. 1264-1269, Nov. 1999.
Santoro et al., "Mechanism and Utility of an RNA-Cleaving DNA Enzyme" *Biochemistry*, vol. 37, No. 38, pp. 13330-13342, 1998.

Santoro et al., "A General Purpose RNA-Cleaving DNA Enzyme" *Proc. Natl. Acad. Sci. USA*, vol. 94, pp. 4262-4266, Apr. 1997.
Sukhatme. V.P. Human mRNA for early growth response Protein 1 (hEGR1). 1990. Genbank Accession No. X52541.
Perez-Castillo et al "NGFI-A Gene Expression is Necessary for T Lymphocyte Proliferation" Journal of Biological Chemistry, American Society of Biological Chemists, Baltimore, MD, US. vol. 268, No. 26, (Sep. 15, 1993) pp. 19445-19450.
Rupprecht H D et al "Der Transkriptionsfakto EGR-1 Reguliert Das Wachstum Glomerulaerer Mesangiumzellen The Transcriptional Regulator EGR-1 and Growth Control of GL Omerula Mesangial Cells" Medizinische Klinik, vol. 92, No. 2 (1997) pp. 68-73.
Sachinidis Agapios et al "Oligodeoxynucleotides directed to early growth response gene-1 mRNA inhibit DNA synthesis in the smooth muscle cell" European Journal of Pharmacology, vol. 309, No. 1 (1996) pp. 95-105.
DATABASE EMBL 'Online! (Jul. 6, 1989) "Rattus norvegicus nerve growth factor (NGF-IA) gene, complete cds" XP002303013 retrieved from EBI accession No. EM_PRO:RNNGF1A Database accession No. J04154.
Adamis, A. P., et al., "Angiogenesis and Ophthalmic Disease", Angiogenesis, 1999, vol. 3, pp. 9-14.
Bhushan, M., "Recent Advances in Cutaneous Angiogenesis", British Journal of Dermatology, 2002, vol. 147, pp. 418-425.
Dightl, W., et al., "HMG-CoA Reductase Inhibitors Regulate Inflammatory Transcription Factors in human Endothelial and Vascular Smooth Muscle Cells", Arterioscler Thromb Vasc. Biol., Jan. 2003, pp. 58-63.
Fahmy, R. G., et al., "Locked Nucleic Acid Modified DNA Enzymes Targeting Early Growth Response-1 Inhibit Human Vascular Smooth Muscle Cell Growth", Nucleic Acids Research, 2004, vol. 32, No. 7, pp. 2281-2285.
Fahmy, R. G., et al., "Transcription Factor Egr-1 Supports FGF-Dependent Angiogenesis During Neovascularization and Tumor Growth", Nature Medicine, Aug. 2003, vol. 9, No. 8, pp. 1026-1032.
Ferrara, N., "The Biology of VEGF and Its Receptors" Nature Medicine, Jun. 2003, vol. 9, No. 6, pp. 669-676.
Hofer, G., et al., "Transcription Factor Egr-1 Regulates Glomerular Mesangial Cell Proliferation", The Journal of Biological Chemistry, Nov. 8, 1996, vol. 271, No. 45, pp. 28306-28310.
Ito, Y., et al., "Inhibition of Antiogenesis and Vascular Leakiness by Angiopoietin-Related Protein 4" Cancer Research, Oct. 15, 2003, vol. 63, pp. 6651-6657.
Janssen, Y., et al., "Differential Induction of c-*fos*, c-*jun*, and apoptosis in Lung Epithelial Cells Exposed to ROS or RNS", 1997, pp. L789-L796.
Krzystolik, M. G., et al., "Prevention of Experimental Choroidal Neovascularization With Intravitreal Anti-Vascular Endothelial Growth Factor Antibody Fragment", Arch. Ophthalmol., Mar. 2002, vol. 120, pp. 338-346.

*Primary Examiner*—Jon E. Angell
*Assistant Examiner*—Amy H. Bowman
(74) *Attorney, Agent, or Firm*—Browdy and Neimark

(57) ABSTRACT

The present invention relates to DNAzymes which are targeted against mRNA molecules encoding EGR-1 (also known as Egr-1 and NGFI-A). The present invention also relates to compositions including these DNAzymes and to methods of treatment involving administration of the DNAzymes.

29 Claims, 8 Drawing Sheets

OTHER PUBLICATIONS

Kukita, T., et al., "Regulation of Osteoclastogenesis by Antisense Oligodeoxynucleotide Specific to Zinc Finger Nuclear transcription Factors Egr-1 and WT1 in Rat Bone Marrow Culture System", Endocrinology, 1997, vol. 138, No. 10, pp. 4384-4389.

Kurreck, J., et al., "Comparative Study of DNA Enzymes and Ribozymes against the Same Full-length Messenger RNA of the Vanilloid Receptor Subtype I", The Journal of Biological Chemistry, Mar. 1, 2002, vol. 277, No. 9, pp. 7099-7107.

Leenders, W., et al., "Design of a Variant of Vascular Endothelial Growth Factor-A (VEGF-A) Antagonizing KDR/Flk-1 and Flt-1", Laboratory Investigation, Apr. 2002, vol. 82, No. 4, pp. 473-481.

Maldve, R. E., et al., "Tumor-Promoting Activity of 2,4-Dinitrofluorobenzene", Int. Journal Cancer, 1995, vol. 60, pp. 545-553.

Mitchell A., et al., "Inhibition of Human Breast Carcinoma Proliferation, Migration, Chemoinvasion and Solid Tumor Growth by DNAzymes Targeting The Zinc Finger Transcription Factor EGR-1", Nucleic Acids Research, 2004, vol. 32, No. 10, pp. 3065-3069.

Momiyama, N., et al., "Suppression of c-*jun* by Antisense Oligonucleotide Inhibits Cell Adhesion but not Respiratory Burst During Phorbol Ester-Induced Differentiation of U937 Human Monoblastic Cells", Cell Growth & Differentiation, Aug. 1996, vol. 7, pp. 1006-1012.

Nakamura, H., et al., "Introduction of DNA Enzyme for Egr-1 Into Tubulointerstitial Fibroblasts by Electroporation Reduced Interstitial α-smooth Muscle Actin Expression and Fibrosis in Unilateral Ureteral Obstruction (UUO) Rats" Gene Therapy, 2002, vol. 9, pp. 495-502.

Nguyen, H. Q., et al., "The Zinc Finger Transcription Factor Egr-1 Is Essential for and Restricts Differentiation Along the Macrophage Lineage", Cell, Jan. 29, 1993, vol. 72, pp. 197-209.

Pan, W., et al., "Identification of Efficient Cleavage Sites in Long-Target RNAs", Ribozymes and siRNA Protocols Second Edition; Methods in Molecular Biology, 2004, vol. 252, pp. 125-144.

Ross, R., "Atherosclerosis—An Inflammatory Disease" Mechanisms of Disease, Jan. 14, 1999, vol. 340, No. 2, pp. 115-126.

Santoro, S., et al., "A General Purpose RNA-Cleaving DNA Enzyme", Pro. Natl. Acad., Sci. USA, Apr. 1997, vol. 94, pp. 4262-4266.

Scherer, L. J., et al., "Approaches for the Sequence-Specific Knockdown of mRNA", Nature Biotechnology, Dec. 2003, vol. 21, No. 12, pp. 1457-1465.

Sells, S. F., et al., "The Zinc Finger Transcription Factor EGR-1 Impedes Interleukin-1-Inducible Tumor Growth Arrest", Molecular Cellular Biology, Feb. 1995, vol. 15, No. 2, pp. 682-692.

Suggs, S. V., et al., "cDNA Sequence of the Human Cellular Early Growth Response Gene Egr-1", Nucleic Acids Research, Apr. 13, 1990, vol. 18, No. 14, EMBL accession No. X52541, p. 4283.

Van Nieuw Amerongen, G. P., et al., "Targets of Pharmacological Intervention of Endothelial Hyperpermeability and Barrier Function", Vascular Pharmacology, 2003, vol. 39, pp. 257-272.

Wang, N., et al., "Adenovirus-Mediated Overexpression of Dominant-Negative Mutant of C-Jun Prevents Intercellular Adhesion Molecule-1 Inductionn by LDL", Arterioscler Thromb Vasc Biol., Sep. 2001, pp. 1414-1420.

Yamada, M., "Molecular Mechanism and Role of Endothelial Monocyte Chemoattractant Protein-1 Induction by Vascular Endothelial Growth Factor", Arterioscler Thromb Vasc Biol., Nov. 2003, pp. 1996-2001.

Yokota, T., et al., "siRNA-Based Inhibition Specific for Mutant SOD1 with Single Nucleotide Alternation in Familial ALS, Compared with Ribozyme and DNA Enzyme", Biochemical and Biophysical Research Communications, 2004, vol. 314, pp. 283-291.

Zhang, g., et al., "Effect of Deoxyribozymes Targeting c-Jun on Solid Tumor Growth and Angiogenesis in Rodents", Journal of the National Cancer Institute, May 5, 2004, vol. 96, No. 9, pp. 683-696.

\* cited by examiner

CATALYTIC MOLECULES

FIELD OF THE INVENTION

The present invention relates to DNAzymes which are targeted against mRNA molecules encoding EGR-1 (also known as Egr-1 or NGFI-A). The present invention also relates to compositions including these DNAzymes and to methods of treatment involving administration of the DNAzymes.

BACKGROUND OF THE INVENTION

Egr-1 Expression in Smooth Muscle Cells

Smooth muscle cells (SMCs) are well recognized as a significant cellular component of atherosclerotic and post-angioplasty restenotic lesions (Stary et al, 1995; Holmes et al, 1984). SMC migration and proliferation are key events in the pathogenesis of these vascular disorders (Jackson & Schwartz, 1992; Libby et al, 1995). The promoter regions of many genes that encode mitogenic and migratory factors expressed by SMCs in these lesions (Evanko et al, 1998; Murry et al, 1996; Ueda et al, 1996; Tanizawa et al, 1996; Rekhter & Gordon, 1994; Hughes et al, 1993; Brogi et al, 1993; Wilcox et al 1989; Wilcox et al, 1988) contain nucleotide (nt) recognition elements for the nuclear protein and transcription factor, Egr-1 (Khachigian & Collins, 1997; Khachigian et al, 1996). Egr-1 is not expressed in the unmanipulated artery wall, but is rapidly activated by mechanical injury (Khachigian et al, 1996; Silverman et al, 1997; Kim et al, 1995). It is also induced in vascular endothelial cells and/or SMCs exposed to fluid biomechanical forces (Khachigian et al, 1997; Sumpio et al, 1998) and multiple other pathophysiologically-relevant agonists (Delbridge & Khachigian, 1997).

DNAzymes

In human gene therapy, antisense nucleic acid technology has been one of the major tools of choice to inactivate genes whose expression causes disease and is thus undesirable. The anti-sense approach employs a nucleic acid molecule that is complementary to, and thereby hybridizes with, an mRNA molecule encoding an undesirable gene. Such hybridization leads to the inhibition of gene expression.

Anti-sense technology suffers from certain drawbacks. Anti-sense hybridization results in the formation of a DNA/target mRNA heteroduplex. This heteroduplex serves as a substrate for RNAse H-mediated degradation of the target mRNA component. Here, the DNA anti-sense molecule serves in a passive manner, in that it merely facilitates the required cleavage by endogenous RNAse H enzyme. This dependence on RNAse H confers limitations on the design of anti-sense molecules regarding their chemistry and ability to form stable heteroduplexes with their target mRNA's. Anti-sense DNA molecules also suffer from problems associated with non-specific activity and, at higher concentrations, even toxicity.

As an alternative to anti-sense molecules, catalytic nucleic acid molecules have shown promise as therapeutic agents for suppressing gene expression, and are widely discussed in the literature (Haseloff (1988); Breaker (1994); Koizumi (1989); Otsuka; Kashani-Sabet (1992); Raillard (1996); and Carmi (1996)). Thus, unlike a conventional anti-sense molecule, a catalytic nucleic acid molecule functions by actually cleaving its target mRNA molecule instead of merely binding to it. Catalytic nucleic acid molecules can only cleave a target nucleic acid sequence if that target sequence meets certain minimum requirements. The target sequence must be complementary to the hybridizing regions of the catalytic nucleic acid, and the target must contain a specific sequence at the site of cleavage.

Catalytic RNA molecules ("ribozymes") are well documented (Haseloff (1988); Symonds (1992); and Sun (1997)), and have been shown to be capable of cleaving both RNA (Haseloff (1988)) and DNA (Raillard (1996)) molecules. Indeed, the development of in vitro selection and evolution techniques has made it possible to obtain novel ribozymes against a known substrate, using either random variants of a known ribozyme or random-sequence RNA as a starting point (Pan (1992); Tsang (1994); and Breaker (1994)).

Ribozymes, however, are highly susceptible to enzymatic hydrolysis within the cells where they are intended to perform their function. This in turn limits their pharmaceutical applications.

Recently, a new class of catalytic molecules called "DNAzymes" was created (Breaker and Joyce (1995); Santoro (1997)). DNAzymes are single-stranded, and cleave both RNA (Breaker (1994); Santoro (1997)) and DNA (Carmi (1996)). A general model for the DNAzyme has been proposed, and is known as the "10-23" model. DNAzymes following the "10-23" model, also referred to simply as "10-23 DNAzymes", have a catalytic domain of 15 deoxyribonucleotides, flanked by two substrate-recognition domains of seven to nine deoxyribonucleotides each. In vitro analyses show that this type of DNAzyme can effectively cleave its substrate RNA at purine:pyrimidine junctions under physiological conditions (Santoro (1997)).

DNAzymes show promise as therapeutic agents. However, DNAzyme success against a disease caused by the presence of a known mRNA molecule is not predictable. This unpredictability is due, in part, to two factors. First, certain mRNA secondary structures can impede a DNAzyme's ability to bind to and cleave its target mRNA. Second, the uptake of a DNAzyme by cells expressing the target mRNA may not be efficient enough to permit therapeutically meaningful results. For these reasons, merely knowing of a disease and its causative target mRNA sequence does not alone allow one to reasonably predict the therapeutic success of a DNAzyme against that target mRNA, absent an inventive step.

SUMMARY OF THE INVENTION

Accordingly, in a first aspect the present invention provides a DNAzyme which specifically cleaves EGR-1 mRNA, the DNAzyme including
  (i) a catalytic domain which cleaves mRNA at a purine: pyrimidine cleavage site;
  (ii) a first binding domain contiguous with the 5' end of the catalytic domain; and
  (iii) a second binding domain contiguous with the 3' end of the catalytic domain,
  wherein the binding domains are sufficiently complementary to two regions immediately flanking a purine:pyrimidine cleavage site within the region of EGR-1 mRNA corresponding to nucleotides 168 to 332 as shown in SEQ ID NO:1, such that the DNAzyme cleaves the EGR-1 mRNA.

In a second aspect the present invention provides a pharmaceutical composition including a DNAzyme according to the first aspect and a pharmaceutically acceptable carrier.

In a third aspect the present invention provides a method of inhibiting EGR-1 activity in cells which includes exposing the cells to a DNAzyme according to the first aspect of the present invention.

In a fourth aspect the present invention provides a method of inhibiting proliferation or migration of cells in a subject which includes administering to the subject a prophylactically effective dose of a DNAzyme according to the first aspect of the present invention.

In a fifth aspect the present invention provides a method of treating a condition associated with cell proliferation or migration in a subject which includes administering to the subject a prophylactically effective dose of a DNAzyme according to the first aspect of the present invention.

In a sixth aspect the present invention provides an angioplastic stent for inhibiting the onset of restenosis, which comprises an angioplastic stent operably coated with a prophylactically effective dose of a DNAzyme according to the first aspect.

In a seventh aspect, the present invention provides a method for inhibiting the onset of restenosis in a subject undergoing angioplasty, which comprises topically administering a stent according to the fifth aspect to the subject at around the time of the angioplasty.

DETAILED DESCRIPTION OF THE INVENTION

Figure 1:
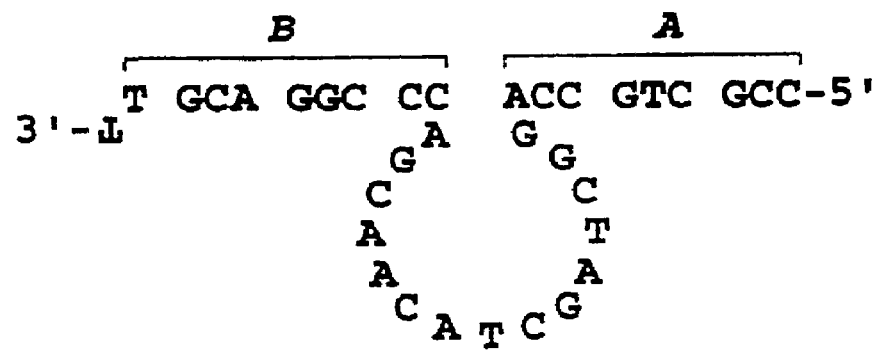
FIG. 1 Sequence of NGFI-ADNAzyme (ED5; SEQ ID NO:21 and SEQ ID NO:22), its scrambled control (ED5SCR; SEQ ID NO:23) and 23 nt synthetic rat substrate. The translational start site is underlined.
Figure 1:
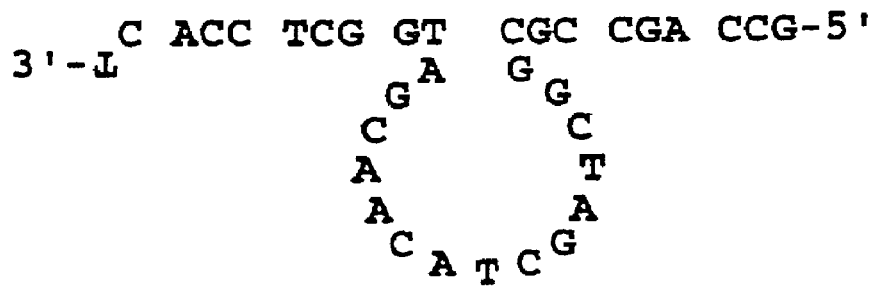

Egr-1 (also known as NGFI-A and EGR-1) binds to the promoters of genes whose products influence cell movement and replication in the artery wall. Table 1 shows an alignment of the human EGR-1 cDNA sequence with the equivalent mouse (Egr-1) and rat (NGFI-A) sequences. The present inventors have now developed DNA-based enzymes that cut NGFI-A/Egr-1/EGR-1 RNA with high efficiency and specificity. The NGFI-A "DNAzyme" cleaved synthetic and in vitro transcribed NGFI-A RNA in a sequence-specific manner and inhibited production of NGFI-A in vascular smooth muscle cells without influencing levels of the related zinc finger protein, Sp1, or the immediate-early gene product, c-Fos. The DNAzyme blocked serum-inducible DNA synthesis in smooth muscle cells and attenuated total cell proliferation. The DNAzyme also inhibited the reparative response to mechanical injury, both in culture and in the rat carotid artery wall. These results indicate a necessary and sufficient role for NGFI-A/Egr-1/EGR-1 in vascular smooth muscle cell growth and provide the first demonstration of a DNAzyme targeted against NGFI-A/Egr-1/EGR-1 transcripts.

Accordingly, in a first aspect the present invention provides a DNAzyme which specifically cleaves EGR-1 mRNA, the DNAzyme including
  (i) a catalytic domain which cleaves mRNA at a purine: pyrimidine cleavage site;
  (ii) a first binding domain contiguous with the 5' end of the catalytic domain; and
  (iii) a second binding domain contiguous with the 3' end of the catalytic domain,
wherein the binding domains are sufficiently complementary to two regions immediately flanking a purine:pyrimidine cleavage site within the region of EGR-1 mRNA corresponding to nucleotides 168 to 332 as shown in SEQ ID NO:1, such that the DNAzyme cleaves the EGR-1 mRNA.

As used herein, "DNAzyme" means a DNA molecule that specifically recognizes and cleaves a distinct target nucleic acid sequence, which may be either DNA or RNA In a preferred embodiment of the first aspect of the present invention, the binding domains are complementary to the regions immediately flanking the cleavage site. It will be appreciated by those skilled in the art, however, that strict complementarity may not be required for the DNAzyme to bind to and cleave the EGR-1 mRNA.

The catalytic domain of a DNAzyme of the present invention may be any suitable catalytic domain. Examples of suitable catalytic domains are described in *Santoro and Joyce,* 1997 and U.S. Pat. No. 5,807,718, the entire contents of which are incorporated herein by reference. In a preferred embodiment, the catalytic domain has the nucleotide sequence GGCTAGCTACAACGA (SEQ ID NO: 2).

Within the parameters of the present invention, the binding domain lengths (also referred to herein as "arm lengths") can be of any permutation, and can be the same or different. In a preferred embodiment, the binding domain lengths are at least 6 nucleotides. Preferably, both binding domains have a combined total length of at least 14 nucleotides. Various permutations in the length of the two binding domains, such as 7+7, 8+8 and 9+9, are envisioned. It is well established that the greater the binding domain length, the more tightly it will bind to its complementary mRNA sequence. Accordingly, in a more preferred embodiment, each domain is nine or more nucleotides in length.

Within the context of the present invention, preferred cleavage sites within the region of EGR-1 mRNA corresponding to nucleotides 168 to 332 are as follows:
(i) the GU site corresponding to nucleotides 198-199;
(ii) the GU site corresponding to nucleotides 200-201;
(iii) the GU site corresponding to nucleotides 264-265;
(iv) the AU site corresponding to nucleotides 271-272;
(v) the AU site corresponding to nucleotides 301-302;
(vi) the GU site corresponding to nucleotides 303-304; and
(vii) the AU site corresponding to nucleotides 316-317.

In a further preferred embodiment, the DNAzyme has a sequence selected from:
(i) 5'-caggggacaGGCTAGCTACAACGAcgttgcggg (SEQ ID NO: 3) targets GU (nt 198, 199); arms hybridise to bp 189-207
(ii) 5'-tgcaggggaGGCTAGCTACAACGAaccgttgcg (SEQ ID NO: 4) targets GU (nt 200, 201); arms hybridise to bp 191-209
(iii) 5'-catcctggaGGCTAGCTACAACGAgagcaggct (SEQ ID NO: 5) targets GU (nt 264, 265); arms hybridise to bp 255-273
(iv) 5'-ccgcggccaGGCTAGCTACAACGAcctggacga (SEQ ID NO: 6) targets AU (nt 271, 272); arms hybridise to bp 262-280
(v) 5'-ccgctgccaGGCTAGCTACAACGAcccggacgt (SEQ ID NO: 7) targets AU (nt 271, 272); arms hybridise to bp 262-280
(vi) 5'-gcggggacaGGCTAGCTACAACGAcagctgcat (SEQ ID NO: 8) targets AU (nt 301, 302); arms hybridise to bp 292-310
(vii) 5'-cagcggggaGGCTAGCTACAACGAatcagctgc (SEQ ID NO: 9) targets GU (nt 303, 304); arms hybridise to bp 294-312
(viii) 5'-ggtcagagaGGCTAGCTACAACGActgcagcgg (SEQ ID NO: 10) targets AU (nt 316, 317); arms hybridise to bp 307-325.

In a particularly preferred embodiment, the DNAzyme targets the AU site corresponding to nucleotides 271-272 (ie. the translation start codon).

In a further preferred embodiment, the DNAzyme has the sequence: 5'-ccgcggccaGGCTAGCTACAACGAcctggacga (SEQ ID NO: 6).

In applying DNAzyme-based treatments, it is preferable that the DNAzymes be as stable as possible against degradation in the intra-cellular milieu. One means of accomplishing this is by incorporating a 3'-3' inversion at one or more termini of the DNAzyme. More specifically, a 3'-3' inversion (also referred to herein simply as an "inversion") means the covalent phosphate bonding between the 3' carbons of the terminal nucleotide and its adjacent nucleotide. This type of bonding is opposed to the normal phosphate bonding between the 3' and 5' carbons of adjacent nucleotides, hence the term "inversion". Accordingly, in a preferred embodiment, the 3'-end nucleotide residue is inverted in the binding domain contiguous with the 3' end of the catalytic domain. In addition to inversions, the instant DNAzymes may contain modified nucleotides, Modified nucleotides include, for example, N3'-P5' phosphoramidate linkages, and peptide-nucleic acid linkages. These are well known in the art.

In a particularly preferred embodiment, the DNAzyme includes an inverted T at the 3' position.

As will be appreciated by those skilled in the art, given that DNAzymes of the present invention cleave human EGR-1, similar DNAzymes can be produced to cleave the corresponding mRNA in other species, eg. rat (NGFI-A), mouse (Egr-1) etc. In a further aspect, the present invention provides such DNAzymes.

In a second aspect the present invention provides a pharmaceutical composition including a DNAzyme according to the first aspect and a pharmaceutically acceptable carrier.

In a third aspect the present invention provides a method of inhibiting EGR-1 activity in cells which includes exposing the cells to a DNAzyme according to the first aspect of the present invention.

In a fourth aspect the present invention provides a method of inhibiting proliferation or migration of cells in a subject which includes administering to the subject a prophylactically effective dose of a DNAzyme according to the first aspect of the present invention.

In a fifth aspect the present invention provides a method of treating a condition associated with cell proliferation or migration in a subject which includes administering to the subject a prophylactically effective dose of a DNAzyme according to the first aspect of the present invention.

In preferred embodiments of the third, fourth and fifth aspects of the present invention, the cells are vascular cells, particularly smooth muscle or endothelial cells. The cells may, however, be cells involved in neoplasia, such as tumour cells and the like.

Although the subject may be any animal or human, it is preferred that the subject is a human.

In a preferred embodiment, conditions associated with SMC proliferation (and migration) are selected from post-angioplasty restenosis, vein graft failure, transplant coronary disease and complications associated with atherosclerosis (cerebrovascular infarction (stroke), myocardial infarction (heart attack), hypertension or peripheral vascular disease (gangrene of the extremities).

Within the parameters of the fourth and fifth aspects of the present invention, any suitable mode of administration may be used to administer or deliver the DNAzyme.

In particular, delivery of the nucleic acid agents described may be achieved by one or more of the following methods:
(a) Liposomes and liposome-protein conjugates and mixtures.
(b) Using catheters to deliver intra-luminal formulations of the nucleic acid as a solution or in a complex with a liposome.
(c) Catheter delivery to adventitial tissue as a solution or in a complex with a liposome.
(d) Within a polymer formulation such as polyethylenimine (PEI) or pluronic gels or within ethylene vinyl acetate copolymer (EVAc). The polymer is preferably delivered intra-luminally.
(e) The nucleic acid may be bound to a delivery agent such as a targetting moiety, or any suitable carrier such as a peptide or fatty acid molecule.
(f) Within a viral-liposome complex, such as Sendai virus.
(g) The nucleic acid may be delivered by a double angioplasty balloon device fixed to catheter.
(h) The nucleic acid could be delivered on a specially prepared stent of the Schatz-Palmaz or derivative type. The stent could be coated with a polymer or agent impregnated with nucleic acid that allows controlled release of the molecules at the vessel wall.

In a preferred embodiment, the mode of administration is topical administration. Topical administration may be effected or performed using any of the various methods and delivery systems known to those skilled in the art. The topical administration can be performed, for example, via catheter and topical injection, and via coated stent as discussed below.

Pharmaceutical carriers for topical administration are well known in the art, as are methods for combining same with active agents to be delivered. The following delivery systems, which employ a number of routinely used carriers, are only representative of the many embodiments envisioned for administering the instant composition.

Topical delivery systems include, for example, gels and solutions, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In the preferred embodiment, the pharmaceutically acceptable carrier is a liposome or a biodegradable polymer. Examples of agents which can be used in this invention include the following: (1) CellFectin, 1:1.5 (M/M) liposome formulation of the cationic lipid N,N$^I$,N$^{II}$,N$^{III}$-tetramethyl-N,N$^I$,N$^{II}$,N$^{III}$-tetrapalmitylspermine and dioleoyl phosphatidylethanolamine (DOPE) (GIBCO BRL); (2) Cytofection GSV, 2:1 (M/M) liposome formulation of a cationic lipid and DOPE (Glen Research); (3) DOTAP (N-[1-(2,3-dioleoyloxy)-N,N,N-trimethyl-aimnoniummethylsulfate] (Boehringer Mannheim); (4) Lipofectamine, 3:1 (M/M) liposome formulation of the polycationic lipid DOSPA and the neutral lipid DOPE (GIBCO BRL); (5) FuGENE$^6$ (Roche Molecular Biochemicals); (6) Superfect (Qiagen); and (7) Lipofectamine 2000 (Gibco-life Technologies).

Examples of suitable methods for topical administration of the DNAzymes of the present invention are described in Autieri et al. (1995), Simons et al. (1992), Morishita et al. (1993), Bennett and Schwartz (1995) and Frimerman et al. (1999).

Determining the prophylactically effective dose of the instant pharmaceutical composition can be done based on animal data using routine computational methods. In one embodiment, the prophylactically effective dose contains between about 0.1 mg and about 1 g of the instant DNAzyme. In another embodiment, the prophylactically effective dose contains between about 1 mg and about 100 mg of the instant DNAzyme. In a further embodiment, the prophylactically effective dose contains between about 10 mg and about 50 mg of the instant DNAzyme. In yet a further embodiment, the prophylactically effective does contains about 25 mg of the instant DNAzyme.

In a sixth aspect the present invention provides an angioplastic stent for inhibiting the onset of restenosis, which comprises an angioplastic stent operably coated with a prophylactically effective dose of a DNAzyme according to the first aspect.

Angioplastic stents, also known by other terms such as "intravascular stents" or simple "stents", are well known in the art. They are routinely used to prevent vascular closure due to physical anomalies such as unwanted inward growth of vascular tissue due to surgical trauma. They often have a tubular, expanding lattice-type structure appropriate for their function, and can optionally be biodegradable.

In this invention, the stent can be operably coated with the instant pharmaceutical composition using any suitable means known in the art. Here, "operably coating" a stent means coating it in a way that permits the timely release of the pharmaceutical composition into the surrounding tissue to be treated once the coated stent is administered. Such coating methods, for example, can use the polymer polypyrrole.

In a seventh aspect, the present invention provides a method for inhibiting the onset of restenosis in a subject undergoing angioplasty, which comprises topically administering a stent according to the fifth aspect to the subject at around the time of the angioplasty.

As used herein, administration "at around the time of angioplasty" can be performed during the procedure, or immediately before or after the procedure. The administering can be performed according to known methods such as catheter delivery.

In order that the nature of the present invention may be more clearly understood, preferred forms thereof will now be described with reference to the following non-limiting Figures and Examples.

TABLE 1

```
Symbol comparison table: GenRunData:pileupdna.cmp CompCheck: 6876
     GapWeight: 5.000
GapLengthWeight: 0.300
EGR1align.msf MSF: 4388 Type: N Apr. 7, 1998 12:07 Check: 5107
Name: mouseEGR1 Len: 4388 Check: 8340 Weight: 1.0 (SEQ ID NO:11)
Name: ratEGR1   Len: 4388 Check: 8587 Weight: 1.0 (SEQ ID NO:12)
Name: humanEGR1 Len: 4388 Check: 8180 Weight: 1.00 (SEQ ID NO:1)
NB. THIS IS RAT NGFI-A numbering
```

|  | 1 |  |  |  | 50 |
|---|---|---|---|---|---|
| mouseEgr1 | .......... | .......... | .......... | .......... | .......... |
| ratNGFIA | CCGCGGAGCC | TCAGCTCTAC | GCGCCTGGCG | CCCTCCCTAC | GCGGGCGTCC |
| humanEGR1 | .......... | .......... | .......... | .......... | .......... |

|  | 51 |  |  |  | 100 |
|---|---|---|---|---|---|
| mouseEGR1 | .......... | .......... | .......... | .......... | .......... |
| ratEGR1 | CCGACTCCCG | CGCGCGTTCA | GGCTCCGGGT | TGGGAACCAA | GGAGGGGGAG |
| humanEGR1 | .......... | .......... | .......... | .......... | .......... |

|  | 101 |  |  |  | 150 |
|---|---|---|---|---|---|
| mouseEGR1 | .......... | .......... | .......... | .......... | .......... |
| ratEGR1 | GGTGGGTGCG | CCGACCCGGA | AACACCATAT | AAGGAGCAGG | AAGGATCCCC |
| humanEGR1 | .......... | .......... | .......... | .......... | .......... |

|  | 151 |  |  |  | 200 |
|---|---|---|---|---|---|
| mouseEGR1 | .......... | .......... | .......... | .......... | .......... |
| ratEGR1 | CGCCGGAACA | GACCTTATTT | GGGCAGCGCC | TTATATGGAG | TGGCCCAATA |
| humanEGR1 | .......... | .......... | .......... | .......... | .......... |

TABLE 1-continued

```
                201                                           250
mouseEGR1   .......... .......... .......... .......... ..........
  ratEGR1   TGGCCCTGCC GCTTCCGGCT CTGGGAGGAG GGGCGAACGG GGGTTGGGGC
humanEGR1   .......... .......... .......... .......... ..........

251                                           300
mouseEGR1   .......... .......... .......... .......... ..........
  ratEGR1   GGGGGCAAGC TGGGAACTCC AGGAGCCTAG CCCGGGAGGC CACTGCCGCT
humanEGR1   .......... .......... .......... .......... ..........

301                                           350
mouseEGR1   .......... .......... .......... .......... ..........
  ratEGR1   GTTCCAATAC TAGGCTTTCC AGGAGCCTGA GCGCTCAGGG TGCCGGAGCC
humanEGR1   .......... .......... .......... .......... ..........

351                                           400
mouseEGR1   .......... .......... .......... .......... ..........
  ratEGR1   GGTCGCAGGG TGGAAGCGCC CACCGCTCTT GGATGGGAGG TCTTCACGTC
humanEGR1   .......... .......... .......... .......... ..........

401                                           450
mouseEGR1   .......... .......... .......... .......... ..........
  ratEGR1   ACTCCGGGTC CTCCCGGTCG GTCCTTCCAT ATTAGGGCTT CCTGCTTCCC
humanEGR1   .......... .......... .......... .......... ..........

451                                           500
mouseEGR1   .......... .......... .......... .......... ..........
  ratEGR1   ATATATGGCC ATGTACGTCA CGGCGGAGGC GGGCCCGTGC TGTTTCAGAC
humanEGR1   .......... .......... .......... .......... ..........

501                                           550
mouseEGR1   .......... .......... .......... .......... ..........
  ratEGR1   CCTTGAAATA GAGGCCGATT CGGGGAGTCG CGAGAGATCC CAGCGCGCAG
humanEGR1   .......... .......... .......... .......... ....CCGCAG 551                                           600
mouseEGR1   .....GGGGA GCCGCCGCCG CGATTCGCCG CCGCCGCCAG CTTCCGCCGC
  ratEGR1   AACTTGGGGA GCCGCCGCCG CGATTCGCCG CCGCCGCCAG CTTCCGCCGC
humanEGR1   AACTTGGGGA GCCGCCGCCG CCATCCGCCG CCGCAGCCAG CTTCCGCCGC 601                                           650
mouseEGR1   CGCAAGATCG GCCCCTGCCC CAGCCTCCGC GGCAGCCCTG CGTCCACCAC
  ratEGR1   CGCAAGATCG GCCCCTGCCC CAGCCTCCGC GGCAGCCCTG CGTCCACCAC
humanEGR1   CGCAGGACCG GCCCCTGCCC CAGCCTCCGC AGCCGCGGCG CGTCCACGCC 651                                           700
mouseEGR1   GGGCCGCGGC TACCGCCAGC CTGGGGGCCC ACCTACACTC CCCGCAGTGT
  ratEGR1   GGGCCGCGGC CACCGCCAGC CTGGGGGCCC ACCTACACTC CCCGCAGTGT
humanEGR1   CGCCCGCGCC CAGGGCGAGT CGGGGTCGCC GCCTGCACGC TTCTCAGTGT 701                                           750
mouseEGR1   GCCCCTGCAC CCCGCATGTA ACCCGGCCAA CCCCCGGCGA GTGTGCCCTC
  ratEGR1   GCCCCTGCAC CCCGCATGTA ACCCGGCCAA CATCCGGCGA GTGTGCCCTC
humanEGR1   TCCCC.GCGC CCCGCATGTA ACCCGGCCAG GCCCCGCAA CGGTGTCCCC 751                                           800
mouseEGR1   AGTAGCTTCG GCCCCGGGCT GCGCCCACC. .ACCCAACAT CAGTTCTCCA
  ratEGR1   AGTAGCTTCG GCCCCGGGCT GCGCCCACC. .ACCCAACAT CAGCTCTCCA
humanEGR1   TGCAGCTCCA GCCCCGGGCT GCACCCCCCC GCCCCGACAC CAGCTCTCCA 801                                           850
mouseEGR1   GCTCGCTGGT CCGGGATGGC AGCGGCCAAG GCCGAGATGC AATTGATGTC
  ratEGR1   GCTCGC<u>ACGT CCGGGATGGC AGCGG</u>CCAAG GCCGAGATGC AATTGATGTC
humanEGR1   GCCTGCTCGT CCAGGATGGC CGCGGCCAAG GCCGAGATGC AGCTGATGTC ED5  (rat) arms hybridise to bp 807-825 in rat sequ
            hED5(hum) arms hybridise to bp 262-280 in hum sequ 851                                           900
mouseEGR1   TCCGCTGCAG ATCTCTGACC CGTTCGGCTC CTTTCCTCAC TCACCCACCA
  ratEGR1   TCCGCTGCAG ATCTCTGACC CGTTCGGCTC CTTTCCTCAC TCACCCACCA
humanEGR1   CCCGCTGCAG ATCTCTGACC CGTTCGGATC CTTTCCTCAC TCGCCCACCA 901                                           950
mouseEGR1   TGGACAACTA CCCCAAACTG GAGGAGATGA TGCTGCTGAG CAACGGGGCT
  ratEGR1   TGGACAACTA CCCCAAACTG GAGGAGATGA TGCTGCTGAG CAACGGGGCT
humanEGR1   TGGACAACTA CCCTAAGCTG GAGGAGATGA TGCTGCTGAG CAACGGGGCT
```

TABLE 1-continued

```
             951                                              1000
mouseEGR1   CCCCAGTTCC TCGGTGCTGC CGGAACCCCA GAGGGCAGCG GCGGTAAT..
  ratEGR1   CCCCAGTTCC TCGGTGCTGC CGGAACCCCA GAGGGCAGCG GCGGCAATAA
humanEGR1   CCCCAGTTCC TCGGCGCCGC CGGGGCCCCA GAGGGCAGCG GCAGCAACAG 1001                                              1050
mouseEGR1   .......AGC AGCAGCAGCA CCAGCAGCGG GGGCGGTGGT GGGGGCGGCA
  ratEGR1   CAGCAGCAGC AGCAGCAGCA GCAGCAGCGG GGGCGGTGGT GGGGGCGGCA
humanEGR1   CAGCAGCAGC AGCAGCGGGG GCGGTGGAGG CGGCGGGGGC GGCAGCAACA 1051                                              1100
mouseEGR1   GCAACAGCGG CAGCAGCGCC TTCAATCCTC AAGGGGAGCC GAGCGAACAA
  ratEGR1   GCAACAGCGG CAGCAGCGCT TTCAATCCTC AAGGGGAGCC GAGCGAACAA
humanEGR1   GCAGCAGCAG CAGCAGCACC TTCAACCCTC AGGCGGACAC GGGCGAGCAG 1101                                              1150
mouseEGR1   CCCTATGAGC ACCTGACCAC AG...AGTCC TTTTCTGACA TCGCTCTGAA
  ratEGR1   CCCTACGAGC ACCTGACCAC AGGTAAGCGG TGGTCTGCGC CGAGGCTGAA
humanEGR1   CCCTACGAGC ACCTGACCGC AG...AGTCT TTTCCTGACA TCTCTCTGAA 1151                                              1200
mouseEGR1   TAATGAGAAG GCGATGGTGG AGACGAGTTA TCCCAGCCAA ACGACTCGGT
  ratEGR1   TCCCCCTTCG TGACTACCCT AACGTCCAGT CCTTTGCAGC ACGGACCTGC
humanEGR1   CAACGAGAAG GTGCTGGTGG AGACCAGTTA CCCCAGCCAA ACCACTCGAC 1201                                              1250
mouseEGR1   TGCCTCCCAT CACCTATACT GGCCGCTTCT CCCTGGAGCC CGCACCCAAC
  ratEGR1   ATCTAGATCT TAGGGACGGG ATTGGGATTT CCTCTATTC ..CACACAGC
humanEGR1   TGCCCCCCAT CACCTATACT GGCCGCTTTT CCCTGGAGCC TGCACCCAAC 1251                                              1300
mouseEGR1   AGTGGCAACA CTTTGTGGCC TGAACCCCTT TTCAGCCTAG TCAGTGGCCT
  ratEGR1   TCCAGGGACT TGTGTTAGAG GGATGTCTGG GGACCCCCCA ACCCTCCATC
humanEGR1   AGTGGCAACA CCTTGTGGCC CGAGCCCCTC TTCAGCTTGG TCAGTGGCCT 1301                                              1350
mouseEGR1   CGTGAGCATG ACCAATCCTC CGACCTCTTC ATCCTCGGCG CCTTCTCCAG
  ratEGR1   CTTGCGGGTG CGCGGAGGGC AGACCGTTTG TTTTGGATGG AGAACTCAAG
humanEGR1   AGTGAGCATG ACCAACCCAC CGGCCTCCTC GTCCTCAGCA CCATCTCCAG 1351                                              1400
mouseEGR1   CTGCTTCATC GTCTTCCTCT GCCTCCCAGA GCCCGCCCCT GAGCTGTGCC
  ratEGR1   TTGCGTGGGT GGCT...... .....GGAGT GGGGGAGGGT TTGTTTTGAT
humanEGR1   CGGCCTCCTC CGC...CTCC GCCTCCCAGA GCCCACCCCT GAGCTGCGCA 1401                                              1450
mouseEGR1   GTGCCGTCCA ACGACAGCAG TCCCATCTAC TCGGCTGCGC CCACCTTTCC
  ratEGR1   GAGCAGGGTT GC....CCCC TCCCCCGCGC GCGTTGTCGC GAGCCTTGTT
humanEGR1   GTGCCATCCA ACGACAGCAG TCCCATTTAC TCAGCGGCAC CCACCTTCCC 1451                                              1500
mouseEGR1   TACTCCCAAC ACTGACATTT TTCCTGAGCC CCAAAGCCAG GCCTTTCCTG
  ratEGR1   TGCAGCTTGT TCCCAAGGAA GGGCTGAAAT CTGTCACCAG GGATGTCCCG
humanEGR1   CACGCCGAAC ACTGACATTT TCCCTGAGCC ACAAAGCCAG GCCTTCCCGG 1501                                              1550
mouseEGR1   GCTCGGCAGG CACAGCCTTG CAGTACCCGC CTCCTGCCTA CCCTGCCACC
  ratEGR1   CCGCCCAGGG TAGGGCGCG CATTAGCTGT GGCC.ACTAG GGTGCTGGCG
humanEGR1   GCTCGGCAGG GACAGCGCTC CAGTACCCGC CTCCTGCCTA CCCTGCCGCC 1551                                              1600
mouseEGR1   AAAGGTGGTT TCCAGGTTCC CATGATCCCT GACTATCTGT TTCCACAACA
  ratEGR1   GGATTCCCTC ACCCCGGACG CCTGCTGCGG AGCGCTCTCA GAGCTGCAGT
humanEGR1   AAGGGTGGCT TCCAGGTTCC CATGATCCCC GACTACCTGT TTCCACAGCA 1601                                              1650
mouseEGR1   ACAGGGAGAC CTGAGCCTGG GCACCCCAGA CCAGAAGCCC TTCAGGGTC
  ratEGR1   AGAGGGGGAT CTCTGTTTG CGTCAGCTGT CGAAATGGCT CT......GC
humanEGR1   GCAGGGGGAT CTGGGCCTGG GCACCCCAGA CCAGAAGCCC TTCAGGGCC 1651                                              1700
mouseEGR1   TGGAGAACCG TACCCAGCAG CCTTCGCTCA CTCCACTATC CACTATTAAA
  ratEGR1   CACTGGAGCA GGTCCAGGAA CATTGCAATC TGCTGCTATC AATTATTAAC
humanEGR1   TGGAGAGCCG CACCCAGCAG CCTTCGCTAA CCCCTCTGTC TACTATTAAG 1701                                              1750
mouseEGR1   GCCTTCGCCA CTCAGTCGGG CTCCCAGGAC TTAAAG.... ...GCTCTTA
  ratEGR1   CACATCGAGA GTCAGTGGTA GCCGGGCGAC CTCTTGCCTG GCCGCTTCGG
humanEGR1   GCCTTTGCCA CTCAGTCGGG CTCCCAGGAC CTGAAG.... ...GCCCTCA
```

TABLE 1-continued

```
                1751                                                    1800
mouseEGR1   ATACCACCTA CCAATCCCAG CTCATCA...A ACCCAGCCGC ATGCGCAAGT
   ratEGR1  CTCTCATCGT CCAGTGATTG CTCTCCAGTA ACCAGGCCTC TCTGTTCTCT
 humanEGR1  ATACCAGCTA CCAGTCCCAG CTCATCA...A ACCCAGCCGC ATGCGCAAGT 1801                                                    1850
mouseEGR1   ACCCCAACCG GCCCAGCAAG ACACCCCCCC ATGAACGCCC ATATGCTTGC
   ratEGR1  TTCCTGCCAG AGTCCTTTTC TGACATCGCT CTGAATAACG AGAAG..GCG
 humanEGR1  ATCCCAACCG GCCCAGCAAG ACGCCCCCCC ACGAACGCCC TTACGCTTGC 1851                                                    1900
mouseEGR1   CCTGTCGAGT CCTGCGATCG CCGCTTTTCT CGCTCGGATG AGCTTACCCG
   ratEGR1  CTGGTGGAGA CAAGTTATCC CAGCCAAACT ACCCGGTTGC CTCCCATCAC
 humanEGR1  CCAGTGGAGT CCTGTGATCG CCGCTTCTCC CGCTCCGACG AGCTCACCCG 1901                                                    1950
mouseEGR1   CCATATCCGC ATCCACACAG GCCAGAAGCC CTTCCAGTGT CGAATCTGCA
   ratEGR1  CTATACTGGC CGCTTCTCCC TGGAGCCTGC ACCCAACAGT GGCAACACTT
 humanEGR1  CCACATCCGC ATCCACACAG GCCAGAAGCC CTTCCAGTGC CGCATCTGCA 1951                                                    2000
mouseEGR1   TGCGTAACTT CAGTCGTAGT GACCACCTTA CCACCCACAT CCGCACCCAC
   ratEGR1  TGTGGCCTGA ACCCCTTTTC AGCCTAGTCA GTGGCCTTGT GAGCATGACC
 humanEGR1  TGCGCAACTT CAGCCGCAGC GACCACCTCA CCACCCACAT CCGCACCCAC 2001                                                    2050
mouseEGR1   ACAGGCGAGA AGCCTTTTGC CTGTGACATT TGTGGGAGGA AGTTTGCCAG
   ratEGR1  AACCCTCCAA CCTCTTCATC CTCAGCGCCT TCTCCAGCTG CTTCATCGTC
 humanEGR1  ACAGGCGAAA AGCCCTTCGC CTGCGACATC TGTGGAAGAA AGTTTGCCAG 2051                                                    2100
mouseEGR1   GAGTGATGAA CGCAAGAGGC ATACCAAAAT CCATTTAAGA CAGAAGGACA
   ratEGR1  TTCCTCTGCC TCCCAGAGCC CACCCCTGAG CTGTGCCGTG CCGTCGAACG
 humanEGR1  GAGCGATGAA CGCAAGAGGC ATACCAAGAT CCACTTGCGG CAGAAGGACA 2101                                                    2150
mouseEGR1   AGAAAGCAGA CAAAAGTGTG GTGGCCTCCC CGGCTGC.....CTCTTCACT
   ratEGR1  ACAGCAGTCC CATTTACTCA GCTGCACCCA CCTTTCCTAC TCCCAACACT
 humanEGR1  AGAAAGCAGA CAAAAGTGTT GTGGCCTCTT CGGCCACCTC CTCTCTCTCT 2151                                                    2200
mouseEGR1   .......... .......... CTCTTCTTAC CCATCCCCAG TGGCTACCTC
   ratEGR1  .......... .......... GACATTTTTC CTGAGCCCCA AAGCCAGGCC
 humanEGR1  TCCTACCCGT CCCCGGTTGC TACCTCTTAC CCGTCCCCGG TTACTACCTC 2201                                                    2250
mouseEGR1   CTACCCATCC CCTGCCACCA CCTCATTCCC ATCCCCTGTG CCCACTTCCT
   ratEGR1  TTTCCTGGCT CTGCAGGCAC AGCCTTGCAG TACCCGCCTC CTGCCTACCC
 humanEGR1  TTATCCATCC CCGGCCACCA CCTCATACCC ATCCCCTGTG CCCACCTCCT 2251                                                    2300
mouseEGR1   ACTCCTCTCC TGGCTCCTCC ACCTACCCAT CTCCTGCGCA CAGTGGCTTC
   ratEGR1  TGCCACCAAG GGTGGTTTCC AGGTTCCCAT GATCCCTGAC TATCTGTTTC
 humanEGR1  TCTCCTCTCC CGGCTCCTCG ACCTACCCAT CCCCTGTGCA CAGTGGCTTC 2301                                                    2350
mouseEGR1   CCGTCGCCGT CAGTGGCCAC CACCTTTGCC TCCGTTCC.. ..........
   ratEGR1  CACAACAACA GGGAGACCTG AGCCTGGGCA CCCCAGACCA GAAGCCCTTC
 humanEGR1  CCCTCCCCGT CGGTGGCCAC CACGTACTCC TCTGTTCCC. ..........

2351                                                    2400
mouseEGR1   ....ACCTGC TTTCCCCACC CAGGTCAGCA GCTTCCCGTC TGCGGGCGTC
   ratEGR1  CAGGGTCTGG AGAACCGTAC CCAGCAGCCT TCGCTCACTC CACTATCCAC
 humanEGR1  .....CCTGC TTTCCCGGCC CAGGTCAGCA GCTTCCCTTC CTCAGCTGTC 2401                                                    2450
mouseEGR1   AGCAGCTCCT TCAGCACCTC AACTGGTCTT TCAGACATGA CAGCGACCTT
   ratEGR1  TATCAAAGCC TTCGCCACTC AGTCGGGCTC CCAGGACTTA AAGGCTCTTA
 humanEGR1  ACCAACTCCT TCAGCGCCTC CACAGGGCTT TCGGACATGA CAGCAACCTT 2451                                                    2500
mouseEGR1   TTCTCCCAGG ACAATTGAAA TTTGCTAAAG GGA.......ATAAAG..
   ratEGR1  ATAACACCTA CCAGTCCCAA CTCATCAAAC CCAGCCGCAT GCGCAAGT..
 humanEGR1  TTCTCCCAGG ACAATTGAAA TTTGCTAAAG GGAAAGGGGA AGAAAGGGA 2501                                                    2550
mouseEGR1   .AAAGCAAAG GGAGAGGCAG GAAAGACATA AAGCA...C AGGAGGGAAG
   ratEGR1  .ACCCCAACC GGCCCAGCAA GACACCCCCC CATGAACGCC CGTATGCTTG
```

TABLE 1-continued

```
humanEGR1   AAAGGGAGAA AAAGAAACAC AAGAGACTTA AAGGACAGGA GGAGGAGATG 2551                                               2600
mouseEGR1   AGATGGCCGC AAGAGGGGCC ACCTCTTAGG TCAGATGGAA GATCTCAGAG
  ratEGR1   CCCTGTTGAG TCCTGCGATC GCCGCTTTTC TCGCTCGGAT GAGCTTACAC
humanEGR1   GCCATAGGAG AGGAGGGTT. .CCTCTTAGG TCAGATGGAG GTTCTCAGAG 2601                                               2650
mouseEGR1   CCAAGTCCTT CTACTCACGA GTA..GAAGG ACCGTTGGCC AACAGCCCTT
  ratEGR1   GCCACATCCG CATCCATACA GGC..CAGAA GCCCTTCCAG TGTCGAATCT
humanEGR1   CCAAGTCCTC CCTCTCTACT GGAGTGGAAG GTCTATTGGC CAACAATCCT 2651                                               2700
mouseEGR1   TCACTTACCA TCCCTGCCTC CCCCGTCCTG TTCCCTTTGA CTTCAGCTGC
  ratEGR1   GCATGCGTAA TTTCAGTCGT AGTGACCACC TTACCACCCA CATCCGCACC
humanEGR1   TTCTGCCCAC TTCCCCTTCC CCAATTACTA TTCCCTTTGA CTTCAGCTGC 2701                                               2750
mouseEGR1   CTGAAACAGC CATGTCCAAG TTCTTCACCT CTATCCAAAG GACTTGATTT
  ratEGR1   C..ACACAGG CGAGAAGCCT TTTGCCTGTG ACATTGTGTG GAGAAAGTTT
humanEGR1   CTGAAACAGC CATGTCCAAG TTCTTCACCT CTATCCAAAG AACTTGATTT 2751                                               2800
mouseEGR1   GCATGG.... ..TATTGGAT AAATCATTTC AGTATCCTCT ..........
  ratEGR1   GCCAGGAGTG ATGAACGCAA GAGGCATACC AAAATCCACT TAAGACAGAA
humanEGR1   GCATGGA... ..TTTTGGAT AAATCATTTC AGTATCATCT ..........

2801                                               2850
mouseEGR1   .....CCATC ACATGCCTGG CCCTTGCTCC CTTCAGCGCT AGACCATCAA
  ratEGR1   GGACAAGAAA GCAGACAAAA GTGTCGTGGC CTCCTCAGCT GCCTCTTCCC
humanEGR1   .....CCATCA TATGCCTGAC CCCTTGCTCC CTTCAATGCT AGAAAATCGA 2851                                               2900
mouseEGR1   GTTGGCATAA AGAAAAAAAA ATGGGTTTGG GCCCTCAGAA CCCTGCCCTG
  ratEGR1   TCTCTTCCTA CCCATCCCCA GTGGCTACCT CCTACCCATC CCCCGCCACC
humanEGR1   GTTGGC.... ......AAAAT GGGGTTTGGG CCCCTCAGAG CCCTGCCCTG 2901                                               2950
mouseEGR1   CATCTTTGTA CAGCATCTGT GCCATGGATT TTGTTTTCCT TGGGGTATTC
  ratEGR1   ACCTCATTTC CATCCCCAGT GCCCACCTCT TACTCCTCTC CGGGCTCCTC
humanEGR1   CACCCTTGTA CAGTGTCTGT GCCATGGATT TCGTTTTCT TGGGGTACTC 2951                                               3000
mouseEGR1   TTGATGTGAA GATAATTTGC ATACT..... .CTATTGTAT TATTTGGAGT
  ratEGR1   TACCTACCCG TCTCCTGCAC ACAGTGGCTT CCCATCGCCC TCGGTGGCCA
humanEGR1   TTGATGTGAA GATAATTTGC ATATT..... .CTATTGTAT TATTTGGAGT 3001                                               3050
mouseEGR1   TAAATCCTCA CTTTGGGG.. GAGGGGGGAG CAAAGCCAAG CAAACCAATG
  ratEGR1   CCACCTATGC CTCCGTCC.. CACCTGCTTT CCCTGCCCAG GTCAGCACCT
humanEGR1   TAGGTCCTCA CTTGGGGGAA AAAAAAAAAA AAAAGCCAAG CAAACCAATG 3051                                               3100
mouseEGR1   ATGATCCTCT ATTTTGTGAT GACTCTGCTG TGACATTA.. ..........
  ratEGR1   TCCAGTCTGC AGGGGTCAGC AACTCCTTCA GCACCTCAAC GGGTCTTTCA
humanEGR1   GTGATCCTCT ATTTTGTGAT GATGCTGTGA CAATA..... ..........

3101                                               3150
mouseEGR1   .GGTTTGAAG CATTTTTTTT TTCAAGCAGC AGTCCTAGGT ATTAACTGGA
  ratEGR1   GACATGACAG CAACCTTTTC TCCTAGGACA ATTGAAATTT GCTAAAGGGA
humanEGR1   ...AGTTTGA ACCTTTTTTT TTGAAACAGC AGTCCCAG.. ..TATTCTCA 3151                                               3200
mouseEGR1   ..GCATGTGT CAGAGTGTTG TTCCGTTAAT TTTGTAAATA CTGGCTCGAC
  ratEGR1   ATGAAAGAGA GCAAGGGAG GGGAGCGCGA GAGACAATAA AGGACAGGAG
humanEGR1   GAGCATGTGT GAGAGTGTTG TTCCGTTAAC CTTTTGTAA ATACTGCTTG 3201                                               3250
mouseEGR1   .TGTAACTCT CACATGTGAC AAAGTATGGT TGTTTGGTT GGGTTTTGTT
  ratEGR1   .GGAAGAAAT GGCCCGCAAG AGGGGCTGCC TCTTAGGTCA GATGGAAGAT
humanEGR1   ACCGTACTCT CACATGTGGC AAAATATGGT TGGTTTTTC TTTTTTTTT 3251                                               3300
mouseEGR1   TTTGAGAATT TTTTTGCCCG TCCCTTTGGT TTCAAAAGTT TCACGTCTTG
  ratEGR1   CTCAGAGCCA AGTCCTTCTA GTCAGTAGAA GGCCCGTTGG CCACCAGCCC
humanEGR1   TTGAAAGTGT TTTTTCTTCG TCCTTTTGGT TTAAAAGTT TCACGTCTTG 3301                                               3350
mouseEGR1   GTGCCTTTTG TGTGACACGC CTT.CCGATG GCTTGACATG CGCA......
```

TABLE 1-continued

```
            ratEGR1  TTTCACTTAG CGTCCCTGCC CTC.CCCAGT CCCGGTCCTT TTGACTTCAG
          humanEGR1  GTGCCTTTTG TGTGATGCCC CTTGCTGATG GCTTGACATG TGCAAT....

3351                                            3400
          mouseEGR1  ...GATGTGA GGGACACGCT CACCTTAGCC TTAA...GGG GGTAGGAGTG
            ratEGR1  CTGCCTGAAA CAGCCACGTC CAAGTTCTTC ACCT...CTA TCCAAAGGAC
          humanEGR1  .....TGTGA GGGACATGCT CACCTCTAGC CTTAAGGGGG GCAGGGAGTG 3401                                            3450
          mouseEGR1  ATGTGTTGGG GGAGGCTTGA GAGCAAAAAC GAGGAAGAGG GCTGAGCTGA
            ratEGR1  TTGATTTGCA TGGTATTGGA TAAACCATTT CAGCATCATC TCCACCACAT
          humanEGR1  ATGATTTGGG GGAGGCTTTG GGAGCAAAAT AAGGAAGAGG GCTGAGCTGA 3451                                            3500
          mouseEGR1  GCTTTCGGTC TCCAGAATGT AAGAAGAAAA AATTTAAACA AAAATCTGAA
            ratEGR1  GCCTGGCCCT TGCTCCCTTC AGCACTAGAA CATCAAGTTG GCTGAAAAAA
          humanEGR1  GCTTCGGTTC TCCAGAATGT AAGAAAACAA ATCTAAAAC AAAATCTGAA 3501                                            3550
          mouseEGR1  CTCTCAAAAG TCTATTTTTC TAAACTGAAA ATGTAAATTT ATACATCTAT
            ratEGR1  AAAATGGGTC TGGGCCCTCA GAACCCTGCC CTGTATCTTT GTACA.....
          humanEGR1  CTCTCAAAAG TCTATTTTTT TAA.CTGAAA ATGTAAATTT ATAAATATAT 3551                                            3600
          mouseEGR1  TCAGGAGTTG GAGTGTTGTG GTTACCTACT GAGTAGGCTG CAGTTTTTGT
            ratEGR1  GCATCTGTGC CATGGATTTT GTTTTCCTTG GGTATTCTT GATGTGAAGA
          humanEGR1  TCAGGAGTTG GAATGTTGTA GTTACCTACT GAGTAGGCGG CGATTTTTGT 3601                                            3650
          mouseEGR1  ATGTTATGAA CATGAAGTTC ATTATTTTGT GGTTTTATTT TACTTTGTAC
            ratEGR1  TAATTTGCAT ACTCTATTGT ACTATTTGGA GTTAAATTCT CACTTTGGGG
          humanEGR1  ATGTTATGAA CATGCAGTTC ATTATTTTGT GGTTCTATTT TACTTTGTAC 3651                                            3700
          mouseEGR1  TTGTGTTTGC TTAAACAAAG TAACCTGTTT GGCTTATAAA CACATTGAAT
            ratEGR1  GAGGGGAGC AAAGCCAAGC AAACCAATGG TGATCCTCTA TTTTGTGATG
          humanEGR1  TTGTGTTTGC TTAAACAAAG TGA.CTGTTT GGCTTATAAA CACATTGAAT 3701                                            3750
          mouseEGR1  GCGCTCTATT GCCCATGG.. ..GATATGTG GTGTGTATCC TTCAGAAAAA
            ratEGR1  ATCCTGCTGT GACATTAGGT TTGAAACTTT TTTTTTTTTT TGAAGCAGCA
          humanEGR1  GCGCTTTATT GCCCATGG.. ..GATATGTG GTGTATATCC TTCCAAAAAA 3751                                            3800
          mouseEGR1  TTAAAAGGAA AAAT...... .......... .......... ..........
            ratEGR1  GTCCTAGGTA TTAACTGGAG CATGTGTCAG AGTGTTGTTC CGTTAATTTT
          humanEGR1  TTAAAACGAA AATAAAGTAG CTGCGATTGG G......... ..........

3801                                            3850
          mouseEGR1  .......... .......... .......... .......... ..........
            ratEGR1  GTAAATACTG CTCGACTGTA ACTCTCACAT GTGACAAAAT ACGGTTTGTT
          humanEGR1  .......... .......... .......... .......... ..........

3851                                            3900
          mouseEGR1  .......... .......... .......... .......... ..........
            ratEGR1  TGGTTGGGTT TTTTGTTGTT TTTGAAAAAA AAATTTTTTT TTTGCCCGTC
          humanEGR1  .......... .......... .......... .......... ..........

3901                                            3950
          mouseEGR1  .......... .......... .......... .......... ..........
            ratEGR1  CCTTTGGTTT CAAAAGTTTC ACGTCTTGGT GCCTTTGTGT GACACACCTT
          humanEGR1  .......... .......... .......... .......... ..........

3951                                            4000
          mouseEGR1  .......... .......... .......... .......... ..........
            ratEGR1  GCCGATGGCT GGACATGTGC AATCGTGAGG GGACACGCTC ACCTCTAGCC
          humanEGR1  .......... .......... .......... .......... ..........

4001                                            4050
          mouseEGR1  .......... .......... .......... .......... ..........
            ratEGR1  TTAAGGGGGT AGGAGTGATG TTTCAGGGGA GGCTTTAGAG CACGATGAGG
          humanEGR1  .......... .......... .......... .......... ..........

4051                                            4100
          mouseEGR1  .......... .......... .......... .......... ..........
            ratEGR1  AAGAGGGCTG AGCTGAGCTT TGGTTCTCCA GAATGTAAGA AGAAAAATTT
          humanEGR1  .......... .......... .......... .......... ..........

4101                                            4150
```

TABLE 1-continued

|  |  |  |  |  |  |
|---|---|---|---|---|---|
| mouseEGR1 | .......... | .......... | .......... | .......... | .......... |
| ratEGR1 | AAAACAAAAA | TCTGAACTCT | CAAAAGTCTA | TTTTTTTAAC | TGAAAATGTA |
| humanEGR1 | .......... | .......... | .......... | .......... | .......... |
|  | 4151 |  |  |  | 4200 |
| mouseEGR1 | .......... | .......... | .......... | .......... | .......... |
| ratEGR1 | GATTTATCCA | TGTTCGGGAG | TTGGAATGCT | GCGGTTACCT | ACTGAGTAGG |
| humanEGR1 | .......... | .......... | .......... | .......... | .......... |
|  | 4201 |  |  |  | 4250 |
| mouseEGR1 | .......... | .......... | .......... | .......... | .......... |
| ratEGR1 | CGGTGACTTT | TGTATGCTAT | GAACATGAAG | TTCATTATTT | TGTGGTTTTA |
| humanEGR1 | .......... | .......... | .......... | .......... | .......... |
|  | 4251 |  |  |  | 4300 |
| mouseEGR1 | .......... | .......... | .......... | .......... | .......... |
| ratEGR1 | TTTTACTTCG | TACTTGTGTT | TGCTTAAACA | AAGTGACTTG | TTTGGCTTAT |
| humanEGR1 | .......... | .......... | .......... | .......... | .......... |
|  | 4301 |  |  |  | 4350 |
| mouseEGR1 | .......... | .......... | .......... | .......... | .......... |
| ratEGR1 | AAACACATTG | AATGCGCTTT | ACTGCCCATG | GGATATGTGG | TGTGTATCCT |
| humanEGR1 | .......... | .......... | .......... | .......... | .......... |
|  | 4351 |  | 4388 |  |  |
| mouseEGR1 | .......... | .......... | .......... | ........ |  |
| ratEGR1 | TCAGAAAAAT | TAAAAGGAAA | ATAAAGAAAC | TAACTGGT |  |
| humanEGR1 | .......... | .......... | .......... | ........ |  |

EXAMPLE 1

Characterisation of DNAzymes ED5 and hED5

Materials and Methods

ODN synthesis. DNAzymes were synthesized commercially (Oligos Etc., Inc.) with an inverted T at the 3' position unless otherwise indicated. Substrates in cleavage reactions were synthesized with no such modification. Where indicated ODNs were 5'-end labeled with $\gamma^{32}$P-dATP and T4 polynucleotide kinase (New England Biolabs). Unincorporated label was separated from radiolabeled species by centrifugation on Chromaspin-10 columns (Clontech).

In vitro transcript and cleavage experiments. A $^{32}$P-labelled 206 nt NGFI-A RNA transcript was prepared by in vitro transcription (T3 polymerase) of plasmid construct pJDM8 (as described in Milbrandt, 1987, the entire contents of which are incorporated herein by reference) previously cut with Bgl II. Reactions were performed in a total volume of 20 µl containing 10 mM $MgCl_2$, 5 mM Tris pH 7.5, 150 mM NaCl, 4.8 pmol of in vitro transcribed or synthetic RNA substrate and 60 pmol DNAzyme (1:12.5 substrate to DNAzyme ratio), unless otherwise indicated. Reactions were allowed to proceed at 37° C. for the times indicated and quenched by transferring an aliquot to tubes containing formamide loading buffer (Sambrook et al. 1989). Samples were run on 12% denaturing polyacrylamide gels and autoradiographed overnight at −80° C.

Culture conditions and DNAzyme transfection. Primary rat aortic SMCs were obtained from Cell Applications, Inc., and grown in Waymouth's medium, pH 7.4, containing 10% fetal bovine serum (FBS), 50 µg/ml streptomycin and 50 IU/ml penicillin at 37° C. in a humidified atmosphere of 5% $CO_2$. SMCs were used in experiments between passages 3-7. Pup rat SMCs (WKY12-22 (as described in Lemire et al, 1994, the entire contents of which are incorporated herein by reference)) were grown under similar conditions. Subconfluent (60-70%) SMCs were incubated in serum-free medium (SFM) for 6 h prior to DNAzyme (or antisense ODN, where indicated) transfection (0.1 µM) using Superfect iii accordance with manufacturers instructions (Qiagen). After 18 h, the cells were washed with phosphate-buffered saline (PBS). pH 7.4 prior to transfection a second time in 5% FBS.

Northern blot analysis. Total RNA was isolated using the TRIzol reagent (Life Technologies) and 25 µg was resolved by electrophoresis prior to transfer to Hybond-N+ membranes (NEN-DuPont). Prehybridization, hybridization with $\alpha^{32}$P-dCTP-labeled Egr-1 or β-Actin cDNA, and washing was performed essentially as previously described (Khachigian et al, 1995).

Western blot analysis. Growth-quiescent SMCs in 100 mm plates (Nunc-InterMed) were transfected with ED5 or ED5SCR as above, and incubated with 5% FBS for 1 h. The cells were washed in cold PBS, pH 7.4, and extracted in 150 mM NaCl, 50 mM Tris-HCl, pH 7.5, 1% sodium deoxycholate, 0.1% SDS, 1% Triton X-100, 5 mM EDTA, 1% trasylol, 10 µg/ml leupeptin, 1% aprotinin and 2 mM PMSF. Twenty four µg protein samples were loaded onto 10% denaturing SDS-polyacrylamide gels and electroblotted onto PVDF nylon membranes (NEN-DuPont). Membranes were air dried prior to blocking with non-fat skim milk powder in PBS containing 0.05% (w:v) Tween 20. Membranes were incubated with rabbit antibodies to Egr-1 or Sp1 (Santa Cruz Biotechnology, Inc.) (1:1000) then with HRP-linked mouse anti-rabbit Ig secondary antiserum (1:2000). Where mouse monoclonal c-Fos (Santa Cruz Biotechnology, Inc.) was used, detection was achieved with HRP-linked rabbit anti-mouse Ig. Proteins were visualized by chemiluminescent detection (NEN-DuPont).

Assays of cell proliferation. Growth-quiescent SMCs in 96-well titer plates (Nunc-InterMed) were transfected with ED5 or ED5SCR as above, then exposed to 5% FBS at 37° C. for 72 h. The cells were rinsed with PBS, pH 7.4, trypsinized and the suspension was quantitated using an automated Coulter counter.

Assessment of DNAzyme stability. DNAzymes were 5'-end labeled with $\gamma^{32}$P-dATP and separated from free label by centrifugation. Radiolabeled DNAzymes were incubated in 5% FBS or serum-free medium at 37° C. for the times indicated. Aliquots of the reaction were quenched by transfer to tubes containing formamide loading buffer (Sambrook et al, 1989). Samples were applied to 12% denaturing polyacrylamide gels and autoradiographed overnight at −80° C.

SMC wounding assay. Confluent growth-quiescent SMCs in chamber slides (Nunc-InterMed) were exposed to ED5 or ED5SCR for 18 h prior to a single scrape with a sterile toothpick. Cells were treated with mitomycin C (Sigma) (20 μM) for 2 h prior to injury (Pitsch et al, 1996; Horodyski & Powell, 1996). Seventy-two h after injury, the cells were washed with PBS, pH 7.4, fixed with formaldehyde then stained with hematoxylin-eosin.

Rat arterial ligation model and analysis. Adult male Sprague Dawley rats weighing 300-350 g were anaesthetised using ketamine (60 mg/kg, i.p.) and xylazine (8 mg/kg, i.p.). The right common carotid artery was exposed up to the carotid bifurcation via a midline neck incision. Size 6/0 non-absorbable suture was tied around the common carotid proximal to the bifurcation, ensuring cessation of blood flow distally. A 200 μl solution at 4° C. containing 500 μg of DNAzyme (in DEPC-treated $H_2O$), 30 μl of transfecting agent and Pluronic gel P127 (BASF) was applied around the vessel in each group of 5 rats, extending proximally from the ligature for 12-15 mm. These agents did not inhibit the solidification of the gel at 37° C. After 3 days, vehicle with or without 500 μg of DNAzyme was administered a second time. Animals were sacrificed 18 days after ligation by lethal injection of phenobarbitone, and perfusion fixed using 10% (v:v) formaldehyde perfused at 120 mm Hg. Both carotids were then dissected free and placed in 10% formaldehyde, cut in 2 mm lengths and embedded in 3% (w:v) agarose prior to fixation in paraffin. Five μm sections were prepared at 250 μm intervals along the vessel from the point of ligation and stained with hematoxylin and eosin. The neointimal and medial areas of 5 consecutive sections per rat were determined digitally using a customized software package (Magellan) (Halasz & Martin, 1984) and expressed as a mean ratio per group of 5 rats.

Results and Discussion

The 7×7 nt arms flanking the 15 nt DNAzyme catalytic domain in the original DNAzyme design 7 were extended by 2 nts per arm for improved specificity (L.-Q. Sun, data not shown) (FIG. 1). The 3' terminus of the molecule was capped with an inverted 3'-3'-linked thymidine (T) to confer resistance to 3'->5' exonuclease digestion. The sequence in both arms of ED5 was scrambled (SCR) without altering the catalytic domain to produce DNAzyme ED5SCR (FIG. 1).

A synthetic RNA substrate comprised of 23 nts, matching nts 805 to 827 of NGFI-A mRNA (FIG. 1) was used to determine whether ED5 had the capacity to cleave target RNA. ED5 cleaved the $^{32}$P-5'-end labeled 23-mer within 10 min. The 12-mer product corresponds to the length between the A(816)-U(817) junction and the 5' end of the substrate (FIG. 1). In contrast, ED5SCR had no demonstrable effect on this synthetic substrate. Specific ED5 catalysis was further demonstrated by the inability of the human equivalent of this DNAzyme (hED5) to cleave the rat substrate over a wide range of stoichiometric ratios. Similar results were obtained using ED5SCR (data not shown) hED5 differs from the rat ED5 sequence by 3 of 18 nts in its hybridizing arms (Table 2). The catalytic effect of ED5 on a $^{32}$P-labeled 206 nt fragment of native NGFI-A mRNA prepared by in vitro transcription was then determined. The cleavage reaction produced two radiolabeled species of 163 and 43 nt length consistent with DNAzyme cleavage at the A(816)-U(817) junction. In other experiments, ED5 also cleaved a $^{32}$P-labeled NGFI-A transcript of 1960 nt length in a specific and time-dependent manner (data not shown).

Table 2. DNAzyme Target Sites in mRNA

Similarity between the 18 nt arms of ED5 or hED5 and the mRNA of rat NGFI-A or human EGR-1 (among other transcription factors) is expressed as a percentage. The target sequence of ED5 in NGFI-A mRNA is 5'-807-A CGU CCG GGA UGG CAG CGG-825-3' (SEQ ID NO: 13) (rat NGFI-A sequence), and that of hED5 in EGR-1 is 5'-262-U CGU CCA GGA UGG CCG CGG-280-3' (SEQ ID NO: 14) (Human EGR-1 sequence). Nucleotides in bold indicate mismatches between rat and human sequences. Data obtained by a gap best fit search in ANGIS using sequences derived from Genbank and EMBL. Rat sequences for Sp1 and c-Fos have not been reported.

| Gene | Accession number | Best homology over 18 nts (%) | |
|---|---|---|---|
| | | ED5 | hED5 |
| Rat NGFI-A | M18416 | 100 | 84.2 |
| Human EGR-1 | X52541 | 84.2 | 100 |
| Murine Sp1 | AF022363 | 66.7 | 66.7 |
| Human c-Fos | K00650 | 66.7 | 66.7 |
| Murine c-Fos | X06769 | 61.1 | 66.7 |
| Human Sp1 | AF044026 | 38.9 | 28.9 |

Figure 2:
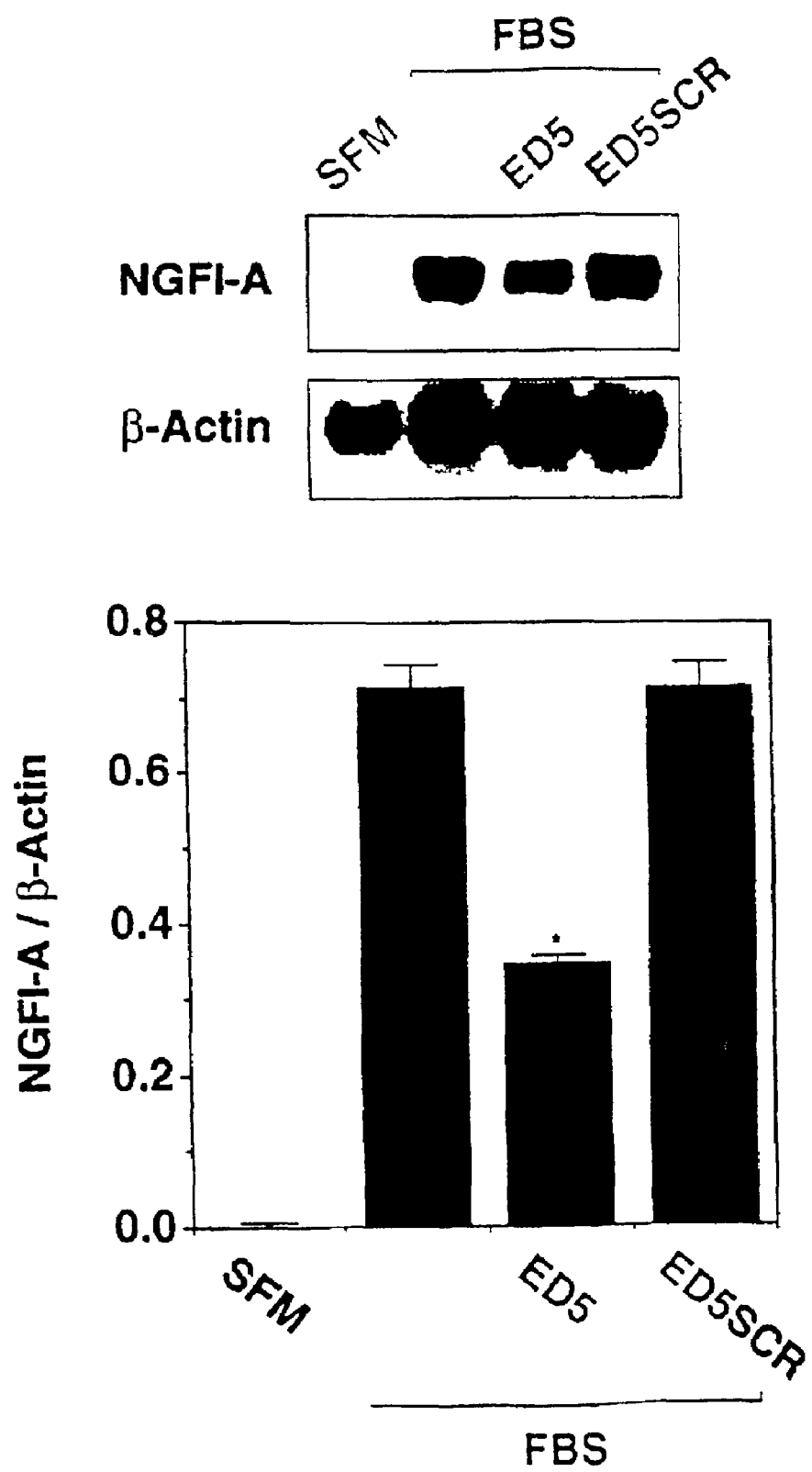
FIG. 2 NGFI-A DNAzyme inhibits the induction of NGFI-A mRNA and protein by serum. Northern blot analysis was performed with 25 μg of total RNA. The blot was stripped and reprobed for β-Actin. Autoradiograms were analyzed by scanning densitometry and the ordinate axis is expressed as NGFI-A band intensity as a fraction of β-Actin band intensity. The mean and standard errors of the mean are indicated in the figure. Data is representative of 2 independent experiments. * indicates P<0.05 (Student's paired t-test) as compared to control (FBS alone).

To determine the effect of the DNAzymes on endogenous levels of NGFI-A mRNA, growth-quiescent SMCs were exposed to ED5 prior to stimulation with serum. Northern blot and densitometric analysis revealed that ED5 (0.1 μM) inhibited serum-inducible steady-state NGFI-A mRNA levels by 55% (FIG. 2a), whereas ED5SCR had no effect (FIG. 2a). The capacity of ED5 to inhibit NGFI-A synthesis at the level of protein was assessed by Western blot analysis. Serum-induction of NGFI-A protein was suppressed by ED5. In contrast, neither ED5SCR nor EDC, a DNAzyme bearing an identical catalytic domain as ED5 and ED5SCR but flanked by nonsense arms had any influence on the induction of NGFI-A (data not shown). ED5 failed to affect levels of the constitutively expressed, structurally-related zinc-finger protein, Sp1. It was also unable to block serum-induction of the immediate-early gene product, c-Fos whose induction, like NGFI-A, is dependent upon serum response elements in its promoter and phosphorylation mediated by extracellular-signal regulated kinase (Treisman, 1990, 1994 and 1995; Gashler & Sukhatme, 1995). These findings, taken together, demonstrate the capacity of ED5 to inhibit production of NGFI-A mRNA and protein in a gene-specific and sequence-specific manner, consistent with the lack of significant homology between its target site in NGFI-A mRNA and other mRNA (Table 2).

Figure 3A:
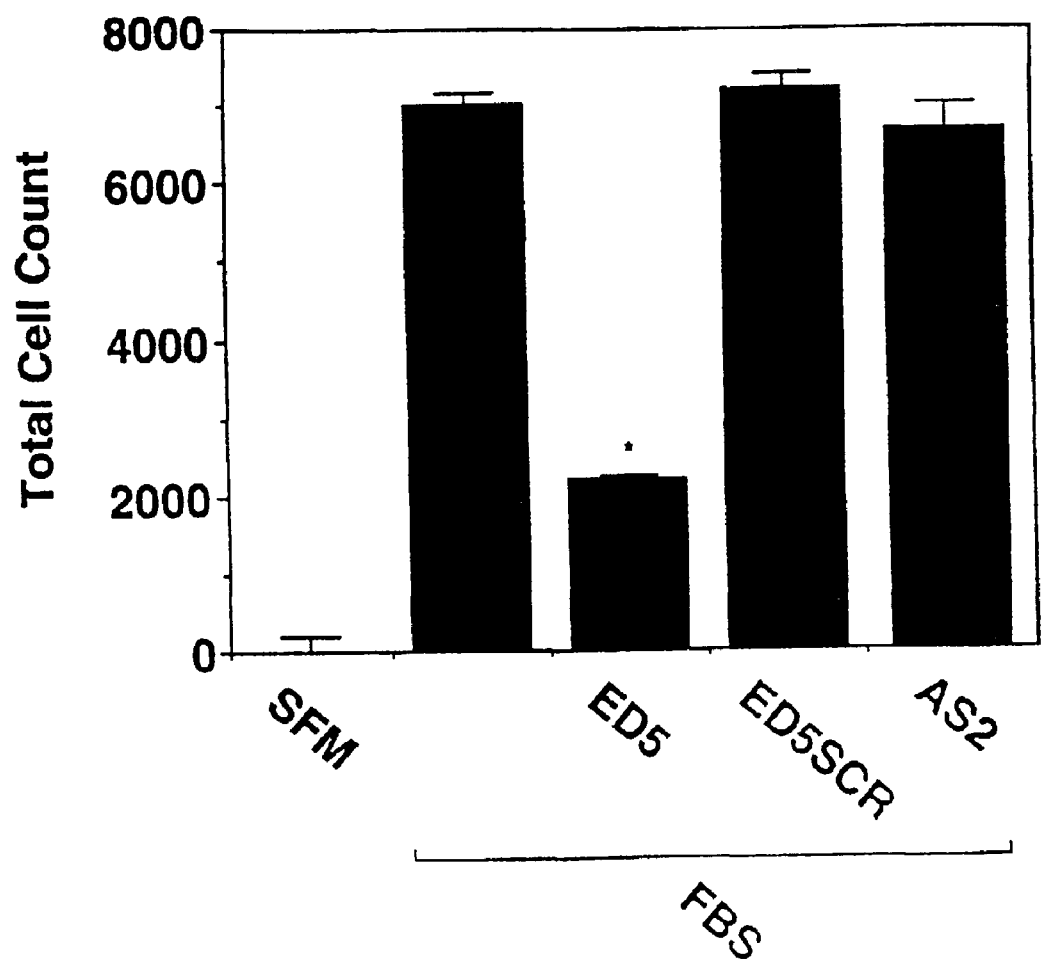
FIG. 3 SMC proliferation is inhibited by NGFI-A DNAzyme. a, Assessment of total cell numbers by Coulter counter. Growth-arrested SMCs that had been exposed to serum and/or DNAzyme for 3 days were trypsinized followed by quantitation of the suspension. The sequence of AS2 is 5'-CTT GGC CGC TGC CAT-3' (SEQ ID NO: 20). b, Proportion of cells incorporating Trypan Blue after exposure to serum and/or DNAzyme. Cells were stained incubated in 0.2% (w:v) Trypan Blue at 22° C. for 5 min prior to quantitation by hemocytometer in a blind manner. c, Effect of ED5 on pup SMC proliferation. Growth-arrested WKY12-22 cells exposed to serum and/or DNAzyme for 3 days were resuspended and numbers were quantitated by Coulter counter. Data is representative of 2 independent experiments performed in triplicate. The mean and standard errors of the mean are indicated in the figure. * indicates P<0.05 (Student's paired t-test) as compared to control (FBS alone).
Figure 3B:
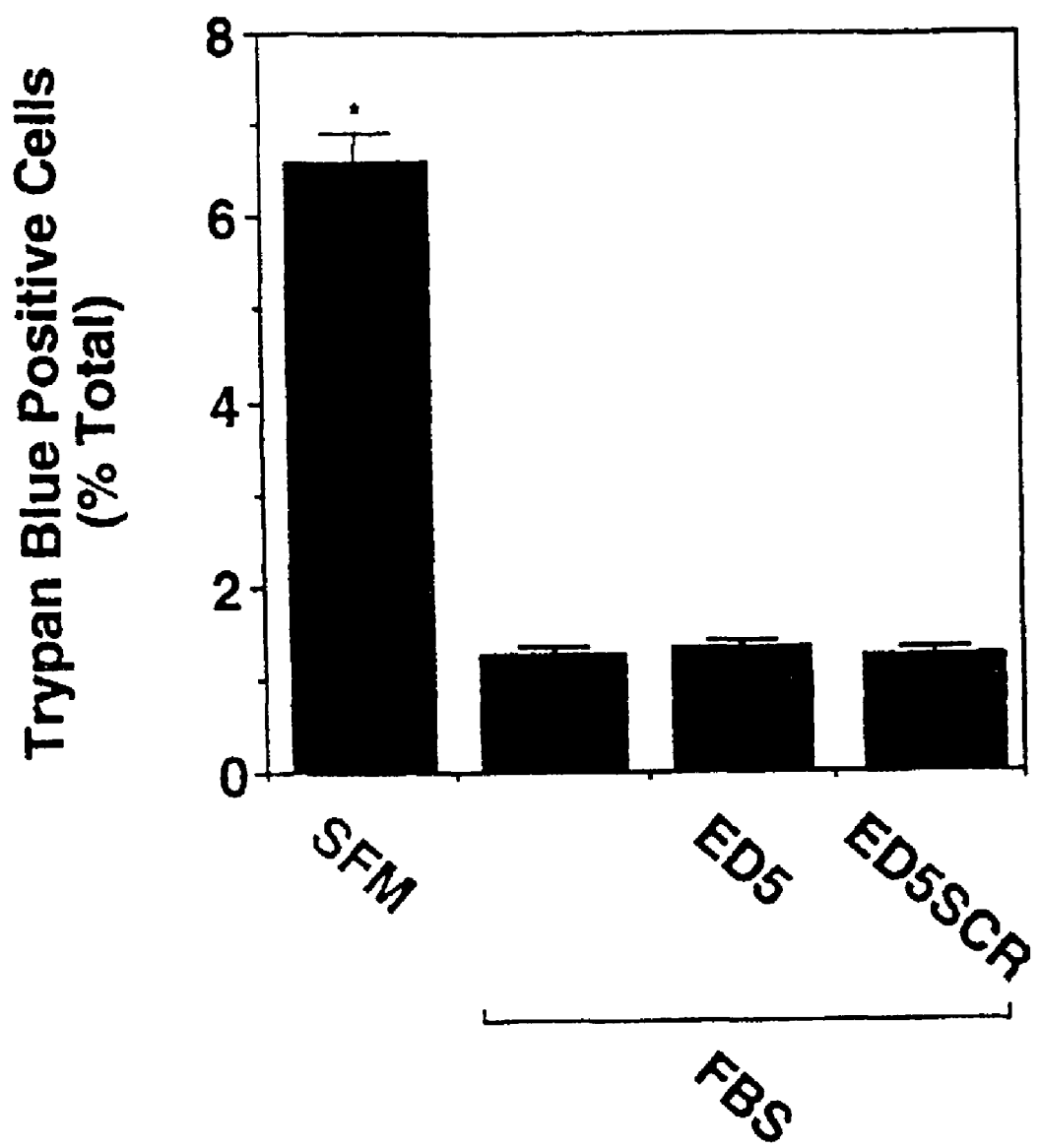

The effect of ED5 on SMC replication was then determined. Growth-quiescent SMCs were incubated with DNAzyme prior to exposure to serum and the assessment of cell numbers after 3 days. ED5 (0.1 μM) inhibited SMC proliferation stimulated by serum by 70% (FIG. 3a). In contrast, ED5SCR failed to influence SMC growth (FIG. 3a). AS2, an antisense NGH-A ODN able to inhibit SMC growth at 1 μM failed to inhibit proliferation at the lower concentration (FIG. 3a). Additional experiments revealed that ED5 also blocked serum-inducible $^3$H-thymidine incorporation into DNA (data not shown). ED5 inhibition was not a consequence of cell death since no change in morphology was observed, and the proportion of cells incorporating Trypan Blue in the presence of serum was not influenced by either DNAzyme (FIG. 3b).

Figure 3C:
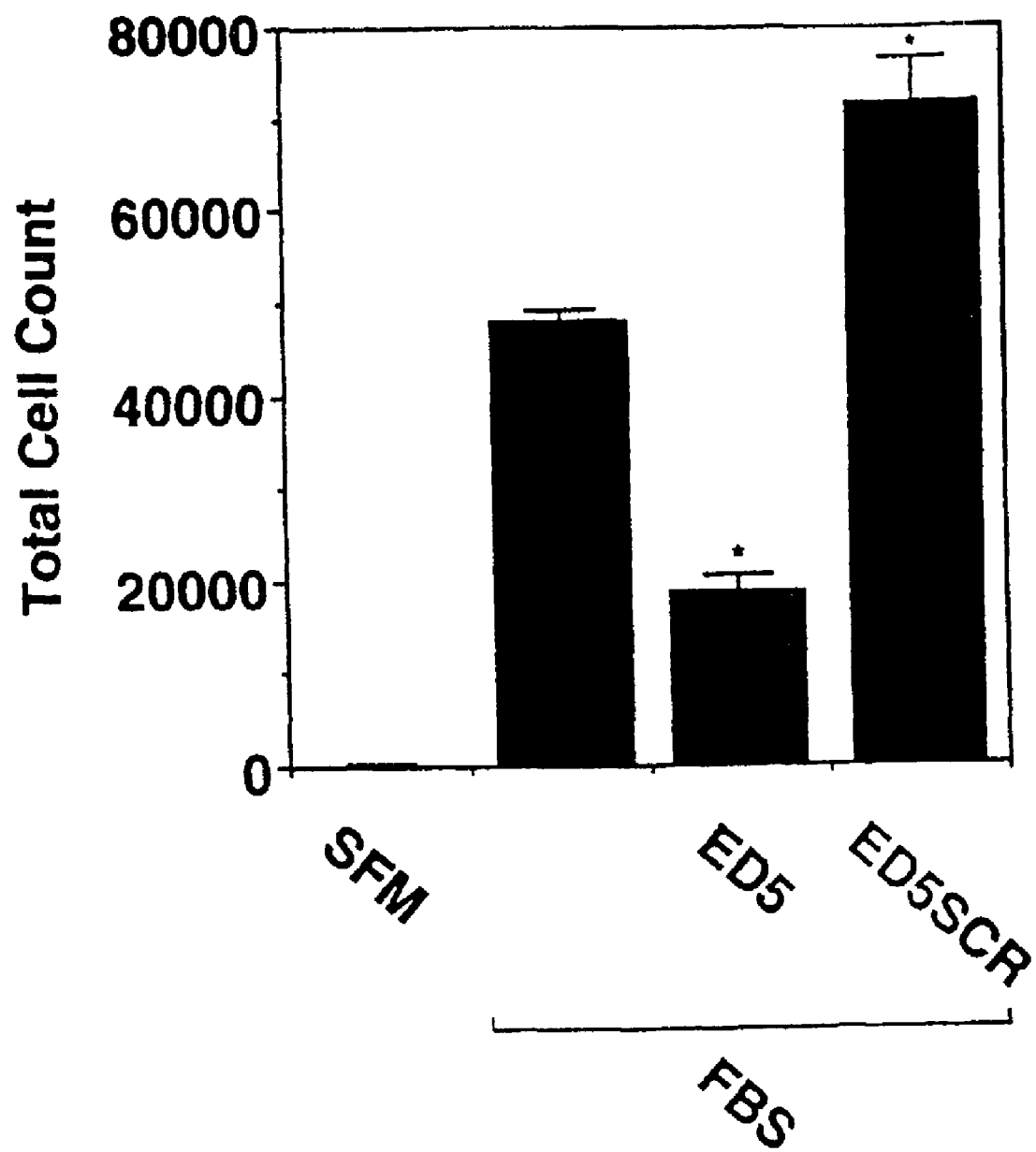

Cultured SMCs derived from the aortae of 2 week-old rats (WKY12-22) are morphologically and phenotypically similar to SMCs derived from the neointima of balloon-injured rat arteries (Seifert et al, 1984; Majesky et al, 1992). The epitheloid appearance of both WKY12-22 cells and neointimal cells contrasts with the elongated, bipolar nature of SMCs derived from normal quiescent media (Majesky et al, 1988). WKY12-22 cells grow more rapidly than medial SMCs and overexpress a large number of growth-regulatory molecules (Lemire et al, 1994), such as NGFI-A (Rafty & Khachigian, 1998), consistent with a "synthetic" phenotype (Majesky et al, 1992; Campbell & Campbell, 1985). ED5 attenuated serum-inducible WKY12-22 proliferation by approximately 75% (FIG. 3c). ED5SCR had no inhibitory effect; surprisingly, it appeared to stimulate growth (FIG. 3c). Trypan Blue exclusion revealed that DNAzyme inhibition was not a consequence of cytotoxicity (data not shown).

To ensure that differences in the biological effects of ED5 and ED5SCR were not the consequence of dissimilar intracellular localization, both DNAzymes were 5'-end labeled with fluorescein isothiocyanate (FITC) and incubated with SMCs. Fluorescence microscopy revealed that both FITC-ED5 and FITC-ED5SCR localized mainly within the nuclei. Punctate fluorescence in this cellular compartment was independent of DNAzyme sequence. Fluorescence was also observed in the cytoplasm, albeit with less intensity. Cultures not exposed to DNAzyme showed no evidence of autofluorescence.

Both molecules were 5'-end labeled with $\gamma^{32}$P-dATP and incubated in culture medium to ascertain whether cellular responsiveness to ED5 and ED5SCR was a consequence of differences in DNAzyme stability. Both $^{32}$P-ED5 and $^{32}$P-ED5SCR remained intact even after 48 h. In contrast to $^{32}$P-ED5 bearing the 3' inverted T, degradation of $^{32}$P-ED5 bearing its 3' T in the correct orientation was observed as early as 1 h. Exposure to serum-free medium did not result in degradation of the molecule even after 48 h. These findings indicate that inverse orientation of the 3' base in the DNAzyme protects the molecule from nucleolytic cleavage by components in serum.

Physical trauma imparted to SMCs in culture results in outward migration from the wound edge and proliferation in the denuded zone. We determined whether ED5 could modulate this response to injury by exposing growth-quiescent SMCs to either DNazyme and Mitomycin C, an inhibitor of proliferation (Pitsch et al, 1996; Horodyski & Powell, 1996) prior to scraping. Cultures in which DNAzyme was absent repopulated the entire denuded zone within 3 days. ED5 inhibited this reparative response to injury and prevented additional growth in this area even after 6 days (data not shown). That ED5SCR had no effect in this system further demonstrates sequence-specific inhibition by ED5.

Figure 4:
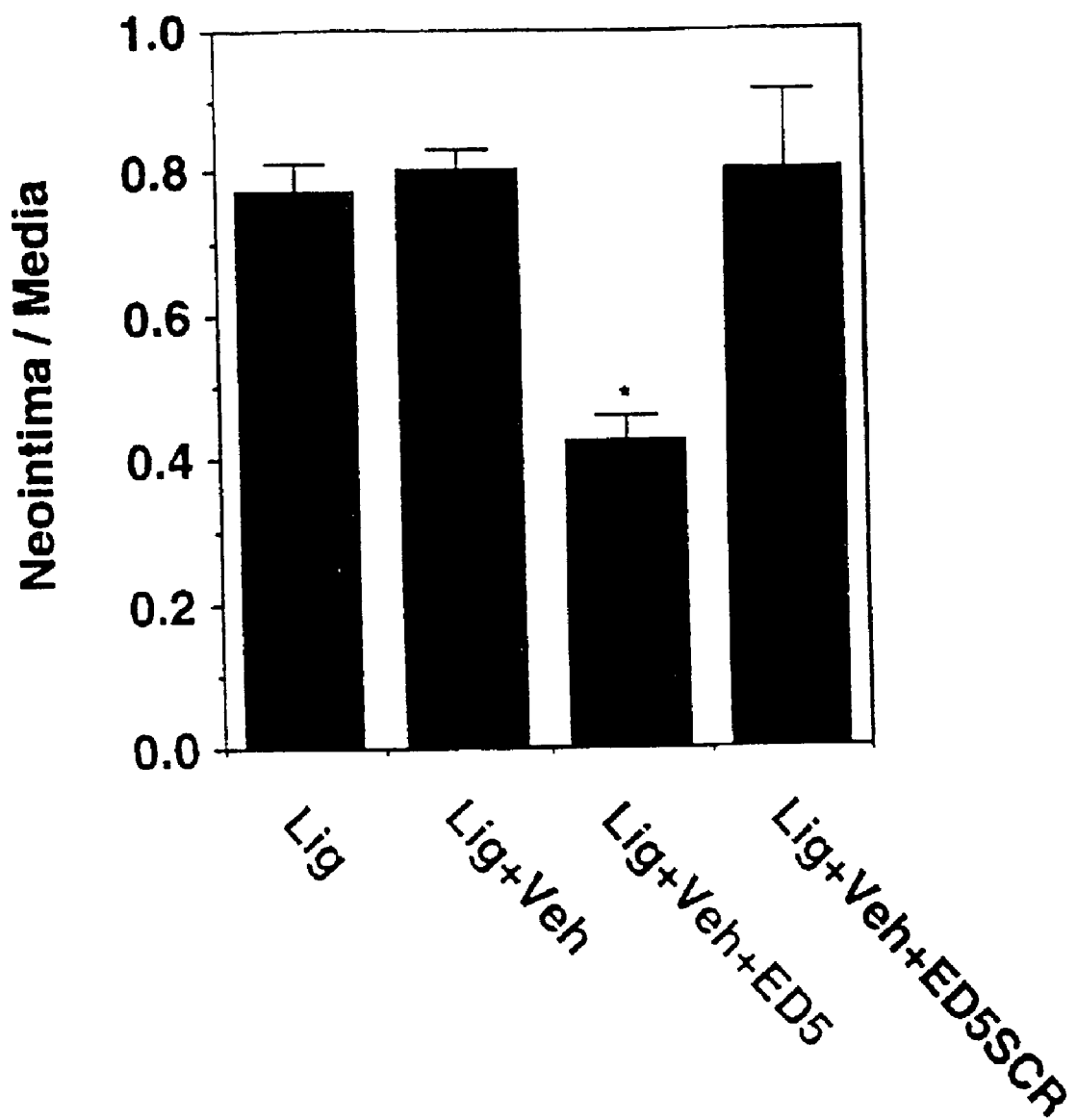
FIG. 4 NGFI-A DNAzyme inhibition of neointima formation in the rat carotid artery. Neointimal and medial areas of 5 consecutive sections per rat (5 rats per group) taken at 250 μm intervals from the point of ligation were determined digitally and expressed as a ratio per group. The mean and standard errors of the mean are indicated by the ordinate axis. * denotes P<0.05 as compared to the Lig, Lig+Veh or Lig+Veh+ED5SCR groups using the Wilcoxen rank sum test for unpaired data. Lig denotes ligation, Veh denotes vehicle.

The effect of ED5 on neointima formation was investigated in a rat model. Complete ligation of the right common carotid artery proximal to the bifurcation results in migration of SMCs from the media to the intima where proliferation eventually leads to the formation of a neointima (Kumar & Lindner, 1997; Bhawan et al, 1977; Buck, 1961). Intimal thickening 18 days after ligation was inhibited 50% by ED5 (FIG. 4). In contrast, neither its scrambled counterpart (FIG. 4) nor the vehicle control (FIG. 4) had any effect on neointima formation. These findings demonstrate the capacity of ED5 to suppress SMC accumulation in the vascular lumen in a specific manner, and argue against inhibition as a mere consequence of a "mass effect" (Kitze et al, 1998; Tharlow et al, 1996).

Further experiments revealed the capacity of hED5 to cleave (human) EGR-1 RNA. hED5 cleaved its substrate in a dose-dependent manner over a wide range of stoichiometric ratios. hED5 also cleaved in a time-dependent manner, whereas hED5SCR, its scrambled counterpart, had no such catalytic property (data not shown).

The specific, growth-inhibitory properties of ED5 reported herein suggest that DNAzymes may be useful as therapeutic tools in the treatment of vascular disorders involving inappropriate SMC growth.

EXAMPLE 2

Cleavage of Human EGR-1 RNA by Panel of Candidate DNAzymes

To evaluate which specific DNAzymes targeting human EGR-1 (other than hED5) efficiently cleave EGR-1 RNA, we prepared in vitro transcribed 35S-labeled EGR-1 RNA and incubated this substrate with candidate DNAzymes for various times. The EGR-1 plasmid template (hs164) was prepared by subcloning bps 168-332 of human EGR-1 into pGEM-T-easy. A 388 nt 35S-labeled substrate was prepared by in vitro transcription using SP6 polymerase. Time-dependent cleavage of the substrate was tested using the following DNZzymes:

DzA: 5'-CAGGGGACAGGCTAGCTACAACGACGT-TGCGGG-X-3' (SEQ ID NO: 15);

DzB: 5'-TGCAGGGGAGGCTAGCTACAACGAAC-CGTTGCG-X-3' (SEQ ID NO: 16);

DzC: 5'-CATCCTGGAGGCTAGCTACAACGAGAG-CAGGCT-X-3' (SEQ ID NO: 17);

DzE: 5'-TCAGCTGCAGGCTAGCTACAACGACTCG-GCCTT-X-3' (SEQ ID NO: 18); and

DzF: 5'-GCGGGGACAGGCTAGCTACAACGA-CAGCTGCAT-X-3' (SEQ ID NO: 19)

where X denotes a 3'-3-linked T.

The DNAzyme that cleaved most effectively of this group was DzA, then DzB, then DzC. In contrast, DzE was inactive.

EXAMPLE 3

Inhibition of Induction of EGR-1 in Human SMC by DzA

To determine whether DzA could block the induction of endogenous human EGR-1, we incubated growth-quiescent human aortic smooth muscle cells with 5% fetal bovine serum and observed the production of EGR-1 protein by Western blot analysis. This band representing the EGR-1 protein was blocked by 0.5 μM DzA, delivered using FuGENE6 (Roche Molecular Biochemicals) and unaffected by DzE. The blot was then stripped and reprobed with antibodies to the transcription factor Sp1. Results obtained showed that neither serum nor DzA affected induction of Sp1. A Coomassie Blue gel indicated that equal protein had been loaded.

The data demonstrate that DzA cleaves EGR-1 mRNA and blocks the induction of EGR-1 protein.

EXAMPLE 4

Inhibition of Human SMC Proliferation by DzA

Figure 5:
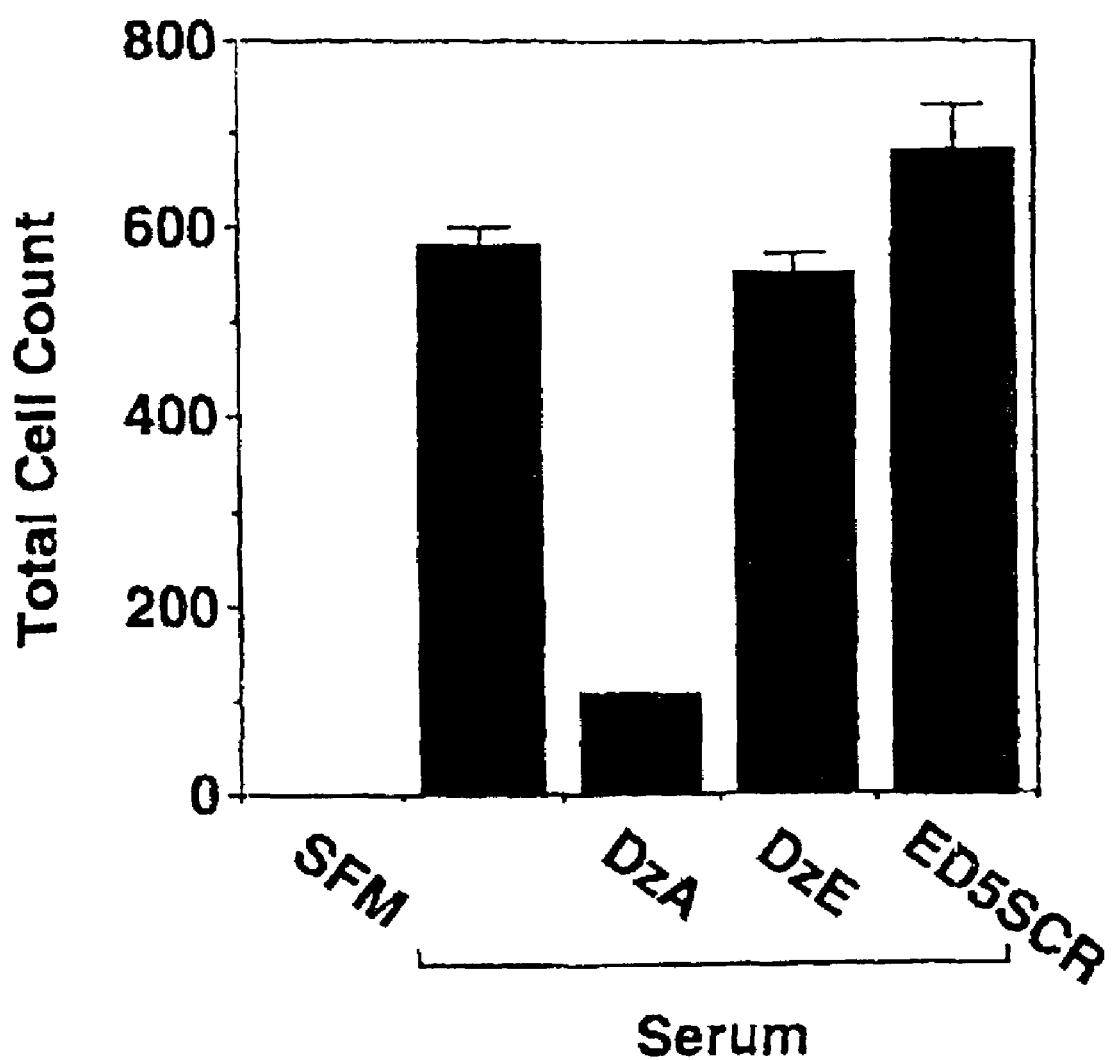
FIG. 5 Selective inhibition of human smooth muscle cell proliferation by DzA.

To ascertain whether proliferation of human SMCs could be inhibited by DzA, a population of SMCs was quantitated with and without exposure to DzA or DzE. SMC proliferation stimulated by 5% fetal bovine serum was significantly inhibited by 0.5 µM DzA (FIG. 5). In contrast, neither DzE nor ED5SCR had any effect (FIG. 5). These data demonstrate that DzA inhibits human SMC proliferation.

EXAMPLE 5

Inhibition of Porcine SMC Proliferation by DzA

Figure 6:
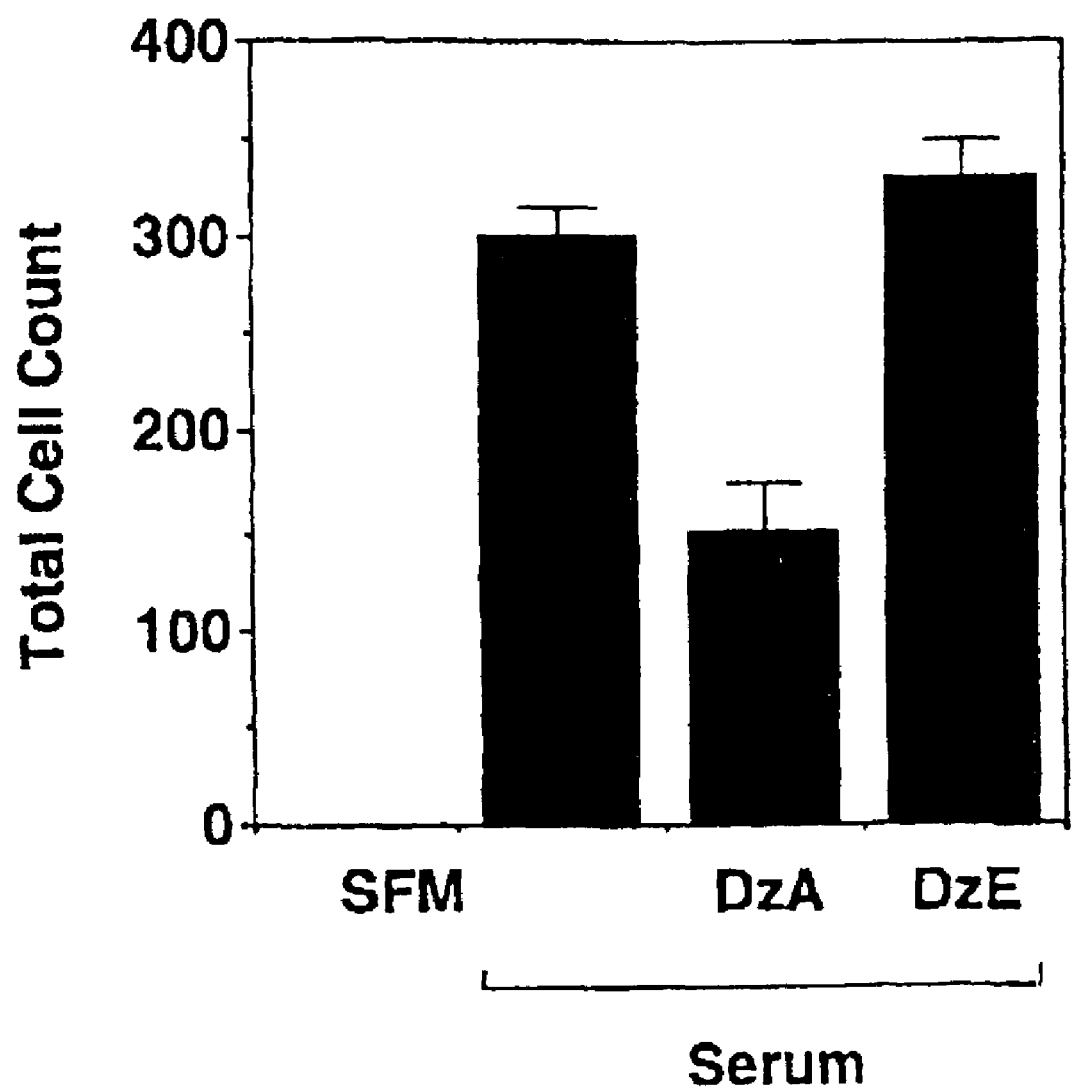
FIG. 6 Specific inhibition of porcine retinal smooth muscle cell proliferation by DzA.

The porcine and human EGR-1 sequences are remarkably well conserved (91%). Porcine retinal SMCs were used to determine whether DzA could block the growth of porcine SMCs. Our studies indicate that DzA (0.5 µM) could inhibit the proliferation of these cells (FIG. 6). In contrast, DzE had no effect (FIG. 6).

EXAMPLE 6

Delivery of DNAzyme into the Porcine Coronary Artery Wall

Porcine angioplasty and stenting are accepted models of human in-stent restenosis (Karas et al. 1992). The porcine coronary anatomy, dimensions and histological response to stenting are similar to the human (Muller et al. 1992). The Transport Catheter has previously been used to deliver antisense DNA targeting c-myc in humans (Serrys et al. 1998) and the pig (Gunn & Cumberland, 1996) via the intraluminal route. Using this catheter, FITC-labeled DNAzyme was applied to the inner wall of a porcine coronary artery, ex vivo, from a newly explanted pig heart. DNAzyme (1000 µg) was delivered via the catheter in 2 ml MilliQ H2O containing 300 µl FuGENE6 and 1 mM $MgCl_2$. The FITC-labeled DNAzyme localised into the intimal cells of the vessel wall. These studies demonstrate that DNAzyme can be delivered to cells within the artery wall via an intraluminal catheter.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. In addition, various documents are cited throughout this application. The disclosures of these documents are hereby incorporated by reference into this application to describe more fully the state of the art to which this invention pertains.

REFERENCES

Autieri, M. V. et al (1995) Antisense oligonucleotides to the P65 subunit of NF-κB inhibit human vascular smooth muscle cell adherence and proliferation and prevent neointiima formation in rat carotid arteries. Biochem; and Biophys. Res. Commun. 213:827-836.

Bennett, M. D. and Schwartz, S. M. (1995) Antisense Therapy for Angioplasty Restenosis. Circulation 92:1981-1993.

Bhawan, J., Joris, I., DeGerolami, U. & Majno, G. (1977) Effect of occlusion on large vessels. Am. J. Pathol. 88, 355-380.

Breaker, R. R. and Joyce, G. (1994) Chemistry and Biology 1:223-229.

Breaker, R. R. and Joyce, G. (1995) Chemistry and Biology 2:655-660.

Brogi, E., et al. (1993) Distinct patterns of expression of fibroblast growth factors and their receptors in human atheroma and nonatherosclerotic arteries. J. Clin. Invest. 92, 2408-2418.

Buck, R. C. (1961) Intimal thickening after ligature of arteries. Circ. Res. 9, 418-426.

Campbell, G. R. & Campbell, J. H. (1985) Smooth muscle phenotypic changes in arterial wall homeostasis: implications for the pathogenesis of atherosclerosis. Exp. Mol. Pathol. 42, 139-162.

Carmi, N., et al. (1996) Chemistry and Biology 3:1039-1046.

Delbridge, G. J. & Khachigian, L. M. (1997) FGF-1-induced PDGF A-chain gene expression in vascular endothelial cells involves transcriptional activation by Egr-1. Circ. Res. 81, 282-288.

Evanko, S. P., Raines, E. W., Ross, R., Gold, L. I. & Wight, T. N. (1998) Proteoglycan distribution in lesions of atherosclerosis depends on lesion severity, structural charcteristics, and the proximity of platelet-derived growth factor and transforming growth factor-beta. Am. J. Pathol. 152, 533-546.

Frimerman, A. et al. (1999) Chimeric DNA-RNA Hammerhead Ribozyme to Proliferating Cell Nuclear Antigen Reduces Stent-Induced Stenosis in a Porcine Coronary Model. Circulation 99: 697-703.

Gashler, A. & Sukhatme, V. (1995) Early growth response protein 1 (Egr-1): prototype of a zinc-finger family of transcription factors. Prog. Nucl. Acid Res. 50, 191-224.

Gunn J. and Cumberland D. C. (1996) Dual balloon catheter: seminars in Interventional Cardiology 1:31-33.

Halasz, P. & Martin, P. (1984) A microcomputer-based system for semi-automatic analysis of histological sections. Proc. Royal Microscop. Soc. 19, 312.

Haseloff, J. & Gerlach, W. A. (1988) Simple RNA enzymes with new and highly specific endoribonuclease activities. Nature 334, 585-591.

Holmes, D. R., et al. (1984) Restenosis after percutaneous transluminal coronary angioplasty (PTCA): a report from the PTCA Registry of the National Heart, Lung, and Blood Institute. Am. J. Cardiol. 53, 77C-81C.

Horodyski, J. & Powell, R. J. (1996) Effect of aprotinin on smooth muscle cell proliferation, migration, and extracellular matrix synthesis. J. Surg. Res. 66, 115-118.

Horodyski, J. & Powell, R. J. (1996) Effect of aprotinin on smooth muscle cell proliferation, migration, and extracellular matrix synthesis. J. Surg. Res. 66, 115-118.

Hughes, S. E., Crossman, D. & Hall, P. A. (1993) Expression of basic and acidic fibroblast growth factors and their receptor in normal and atherosclerotic human arteries. Cardiovasc. Res. 27, 1214-1219.

Jackson, C. L. & Schwartz, S. M. (1992) Pharmacology of smooth muscle replication. Hypertension 20, 713-736.

Karas et al. (1992) Coronary intimal proliferation after balloon injury and stenting in the sine: an animal model of restenosis. J. Am. Coll. Cardiol. 20, 467-474.

Kashani-Sabet, M., et al. (1992) Antisense Research and Development 2:3-15.

Khachigian, L. M. & Collins, T. (1997) Inducible expression of Egr-1-dependent genes: a paradigm of transcriptional activation in vascular endothelium. Circ. Res. 81, 457-461.

Khachigian, L. M., et al. (1997) Egr-1 is activated in endothelial cells exposed to fluid shear stress and interacts with a novel shear-stress response element in the PDGF A-chain promoter. Arterioscl. Thromb. Vasc. Biol. 17, 2280-2286.

Khachigian, L. M., Lindner, V., Williams, A. J. & Collins, T. (1996) Egr-1-induced endothelial gene expression: a common theme in vascular injury. Science 271, 1427-1431.

Khachigian, L. M., Williams, A. J. & Collins, T. (1995) Interplay of Sp1 and Egr-1 in the proximal PDGF-A promoter in cultured vascular endothelial cells. J. Biol. Chem. 270, 27679-27686.

Kim, S., et al. (1995) Angiotensin II type 1 receptor blockade inhibits the expression of immediate-early genes and fibronectin in rat injured artery. Circulation 92.88-95.

Kitze, B., et al. (1998) Human CD4+ T lymphocytes recognize a highly conserved epitope of human T lymphotropic virus type 1 (HTLV-1) env gp21 restricted by HLA DRB1*0101. Clin. Exp. Immunol. 111, 278-285.

Koizumi, M., et al. (1989) Nucleic Acids Research 17:7059-7069.

Kumar, A. & Lindner, V. (1997) Remodeling with neointima formation in the mouse carotid artery after cessation of blood flow. Arterioscl. Thromb. Vasc. Biol. 17, 2238-2244.

Lemire, J. M., Covin, C. W., White, S., Giachelli, C. M. & Schwartz, S. M. (1994) Characterization of cloned aortic smooth muscle cells from young rats. Am. J. Pathol. 144, 1068-1081.

Libby, P., Schwartz, S. M., Brogi, E., Tanaka, H. & Clinton, S. (1995) A cascade model for restenosis. Circ. Res. 86 (Suppl. III), 47-52.

Majesky, M. W., Benditt, E. P. & Schwartz, S. M. (1988) Expression and developmental control of platelet-derived growth factor A-chain and B-chain/Sis genes in rat aortic smooth muscle cells. Proc. Natl. Acad. Sci. USA 85, 1524-1528.

Majesky, M. W., Giachelli, C. M., Reidy, M. A. & Schwartz, S. M. (1992) Rat carotid neointimal smooth muscle cells reexpress a developmentally regulated mRNA phenotype during repair of arterial injury. Circ. Res. 71, 759-768.

Milbrandt, J. (1987) A nerve growth factor-induced gene encodes a possible transcriptional regulatory factor. Science 238, 797-799

Morishita, R. et al (1993) Single intraluminal delivery of antisense cdc2 kinase and proliferating-cell nuclear antigen oligonucleotides result in chronic inhibition of neointimal hyperplasia. Proc. Natl. Acad. Sci. USA 90:8474-8478.

Muller D W et al. (1992) Experimental models of coronary artery restenosis. *J. Am. Coll. Cardiol.* 19, 418-432.

Murry, C. E., Bartosek, T., Giachelli, C. M., Alpers, C. E. & Schwartz, S. M. (1996) Platelet-derived growth factor-A mRNA expression in fetal, normal adult, and atherosclerotic human aortas. Circulation 93, 1095-1106

Otsuka, E. and Koizumi, M., Japanese Patent No. 4,235,919.

Pan, T. and Uhlenbeck, O. C. (1996) Biochemistry 31:3887-3895.

Pitsch, R. J., et al. (1996) Inhibition of smooth muscle cell proliferation and migration in vitro by antisense oligonucleotide to c-myb. J. Vasc. Surg. 23, 783-791.

Pitsch, R. J., et al. (1996) Inhibition of smooth muscle cell proliferation and migration in vitro by antisense oligonucleotide to c-myb. J. Vasc. Surg. 23, 783-791.

Raillard, S. A. and Joyce, G. F. (1996) Biochemistry 35:11693-11701.

Rafty, L. A. & Khachigian, L. M. (1998) Zinc finger transcription factors mediate high constitutive PDGF-B expression in smooth muscle cells derived from aortae of newborn rats. J. Biol. Chem. 273, 5758-5764.

Rekhter, M. & Gordon, D. (1994) Does platelet-derived growth factor-A chain stimulate proliferation of arterial mesenchymal cells in human atherosclerostic plaques? Circ. Res. 75, 410-417.

Sambrook, J., Fritsch, E. F. & Maniatis, T. (1989) Molecular cloning: a laboratory manual, Cold Spring Harbor Laboratory Press, Plainview, N.Y.

Santoro, S. W. & Joyce, G. F. (1997) A general purpose RNA-cleaving DNA enzyme. Proc. Natl. Acad. Sci. USA 94, 4262-4266.

Seifert, R. A., Schwartz, S. M. & Bowen-Pope, D. F. (1984) Developmentally regulated production of platelet-derived growth factor-like molecules. Nature 311, 669-671.

Serrys P W et al. (1998) Antisense oligonucleotide against c-myc administered with the Transport Catheter (36-48 holes, 250 µm diameter) for the prevention of in-stent restenosis: results of randomised ITALICS trial. *Circulation:I*1909.

Silverman, E. S., Khachigian, L. M., Lindner, V., Williams, A. J. & Collins, T. (1997) Inducible PDGF A-chain transcription in vascular smooth muscle cells is mediated by Egr-1 displacement of Sp1 and Sp3. Am. J. Physiol. 42, H1415-H1426.

Stary, H. C., et al. (1995) A definition of advanced types of atherosclerotic lesions and a histological classification of atherosclerosis: a report from the Committee on Vascular Lesions of the Council on Atherosclerosis, American Heart Association. Arterioscler. Thromb. Vasc. Biol. 15, 1512-1531.

Sumpio, B. E., et al. (1998) Regulation of PDGF-B by cyclic strain: lack of involvement of the shear-stress responsive element. Arterioscler. Thromb. Vasc. Biol. 18, 349-355.

Sun, L. Q., et al. (1997) Mol. Biotechnology 7:241-251.

Simons, M. et al (1992) Antisense c-myb oligonucleotides inhibit intimal arterial smooth muscle cell accumulation in vivo. Nature 359:67-70.

Symonds, R. H. (1992) Ann. Rev. Biochem. 61:641-671.

Tanizawa, S., Ueda, M., van der Loos, C. M., van der Wal, A. C. & Becker, A. E. (1996) Expression of platelet-derived growth factor B-chain and beta-receptor expression in human coronary arteries after percutaneous transluminal coronary angioplasty: an immunohisochemical study. Heart 75, 549-556

Tharlow, R. J., Hill, D. R. & Woodruff, G. N. (1996) Comparison of the autoradiographic binding distribution of [3H]-gabapentin with excitatory amino acid receptor and amino acid uptake site distributions in rat brain. Brit. J. Pharmacol. 118, 457-465.

Treisman, R. (1995) Journey to the surface of the cell: Fos regulation and the SRE. EMBO J. 14, 4905-4913.

Treisman, R. (1994) Ternary complex factor: growth factor regulated transcriptional activators. Curr. Opin. Genet. Develop. 4, 96-101.

Treisman, R. (1990) The SRE: a growth factor responsive transcriptional regulator. Sem. Cancer Biol. 1, 47-58.

Tsang, J. and Joyce, G. F. (1994) Biochemistry 33:5966-5973.

Ueda, M., et al. (1996) In situ detection of platelet-derived growth factor-A and -B chain mRNA in human coronary arteries after percutaneous transluminal coronary angioplasty. Am. J. Pathol. 149, 831-843.

Wilcox, J. N., Smith, K. M., Schwartz, S. M. & Gordon, D. (1989) Localization of tissue factor in the normal vessel wall and in the atherosclerotic plaque. Proc. Natl. Acad. Sci. USA 86, 2839-2843.

Wilcox, J. N., Smith, K. M., Williams, L. T., Schwartz, S. M. & Gordon, D. (1988) Platelet-derived growth factor mRNA detection in human atherosclerotic plaques by in situ hybridization. J. Clin. Invest. 82, 1134-1143.

---

The invention claimed is:

1. A DNAzyme which specifically cleaves EGR-1 mRNA, the DNAzyme comprising
   (i) a catalytic domain which cleaves mRNA at a purine:pyrimidine cleavage site;
   (ii) a first binding domain continuous with the 5' end of the catalytic domain; and
   (iii) a second binding domain continuous with the 3' end of the catalytic domain,
   wherein the binding domains are sufficiently complementary to the two regions immediately flanking a purine:pyrimidine cleavage site within the region of EGR-1 mRNA corresponding to nucleotides 168-332 as shown in SEQ ID No: 1, such that the DNAzyme cleaves the EGR-1 mRNA.

2. A DNAzyme as claimed in claim 1 wherein the 3'-end nucleotide residue is inverted in the binding domain contiguous with the 3'-end of the catalytic domain.

3. A DNAzyme as claimed in claim 1 in which the cleavage site is selected from the group consisting of (i) the GU site corresponding to nucleotides 198-199;
(ii) the GU site corresponding to nucleotides 200-201;
(iii) the GU site corresponding to nucleotides 264-265;
(iv) the AU site corresponding to nucleotides 271-272;
(v) the AU site corresponding to nucleotides 301-302;
(vi) the GU site corresponding to nucleotides 303-304; and
(vii) the AU site corresponding to nucleotides 316-317.

4. A DNAzyme as claimed in claim 3 in which the cleavage site is the AU site corresponding to nucleotides 271-272.

5. A DNAzyme as claimed in claim 3 wherein the 3'-end nucleotide residue is inverted in the binding domain contiguous with the 3'-end of the catalytic domain.

6. A DNAzyme as claimed in claim 4 wherein the 3'-end nucleotide residue is inverted in the binding domain contiguous with the 31-end of the catalytic domain.

7. A DNAzyme as claimed in claim 1 in which the catalytic domain has the nucleotide sequence GGCTAGCTACAACGA [SEQ. ID. NO:2].

8. A DNAzyme as claimed in claim 7 wherein the 3'-end nucleotide residue is inverted in the binding domain contiguous with the 3'-end of the catalytic domain.

9. A DNAzyme as claimed in claim 7 in which the cleavage site is selected from the group consisting of
(i) the GU site corresponding to nucleotides 198-199;
(ii) the GU site corresponding to nucleotides 200-201;
(iii) the GU site corresponding to nucleotides 264-265;
(iv) the AU site corresponding to nucleotides 271-272;
(v) the AU site corresponding to nucleotides 301-302;
(vi) the GU site corresponding to nucleotides 303-304; and
(vii) the AU site corresponding to nucleotides 316-317.

10. A DNAzyme as claimed in claim 9 in which the cleavage site is the AU site corresponding to nucleotides 271-272.

11. A DNAzyme as claimed in claim 9 wherein the 3'-end nucleotide residue is inverted in the binding domain contiguous with the 3'-end of the catalytic domain.

12. A DNAzyme as claimed in claim 9 wherein the 3'-end nucleotide residue is inverted in the binding domain contiguous with the 3'-end of the catalytic domain.

13. A DNAzyme as claimed in claim 1 wherein each binding domain is nine or more nucleotides in length.

14. A DNAzyme as claimed in claim 13 wherein the 3'-end nucleotide residue is inverted in the binding domain contiguous with the 3'-end of the catalytic domain.

15. A DNAzyme as claimed in claim 13 in which the cleavage site is selected from the group consisting of
(i) the GU site corresponding to nucleotides 198-199;
(ii) the GU site corresponding to nucleotides 200-201;
(iii) the GU site corresponding to nucleotides 264-265;
(iv) the AU site corresponding to nucleotides 271-272;
(v) the AU site corresponding to nucleotides 301-302;
(vi) the GU site corresponding to nucleotides 303-304; and
(vii) the AU site corresponding to nucleotides 316-317.

16. A DNAzyme as claimed in claim 15 in which the cleavage site is the AU site corresponding to nucleotides 271-272.

17. A DNAzyme as claimed in claim 15 wherein the 3'-end nucleotide residue is inverted in the binding domain contiguous with the 3'-end of the catalytic domain.

18. A DNAzyme as claimed in claim 16 wherein the 3'-end nucleotide residue is inverted in the binding domain contiguous with the 3'-end of the catalytic domain.

19. A DNAzyme as claimed in claim 13 in which the catalytic domain has the nucleotide sequence GGCTAGCTACAACGA [SEQ ID NO: 2].

20. A DNAzyme as claimed in claim 19 wherein the 3'-end nucleotide residue is inverted in the binding domain contiguous with the 3'-end of the catalytic domain.

21. A DNAzyme as claimed in claim 19 in which the cleavage site is selected from the group consisting of
(i) the GU site corresponding to nucleotides 198-199;
(ii) the GU site corresponding to nucleotides 200-201;
(iii) the GU site corresponding to nucleotides 264-265;
(iv) the AU site corresponding to nucleotides 271-272;
(v) the AU site corresponding to nucleotides 301-302;
(vi) the GU site corresponding to nucleotides 303-304; and
(vii) the AU site corresponding to nucleotides 316-317.

22. A DNAzyme as claimed in claim 21 in which the cleavage site is the AU site corresponding to nucleotides 271-272.

23. A DNAzyme as claimed in claim 21 wherein the 3'-end nucleotide residue is inverted in the binding domain contiguous with the 3'-end of the catalytic domain.

24. A DNAzyme as claimed in claim 22 wherein the 3'-end nucleotide residue is inverted in the binding domain contiguous with the 3'-end of the catalytic domain.

25. A DNAzyme as claimed in claim 1 which has a sequence selected from the group consisting of:
(i) 5'-caggggacaGGCTAGCTACAACGAcgttgcggg (SEQ ID NO: 3);
(ii) 5'-tgcaggggaGGCTAGCTACAACGAaccgttgcg (SEQ ID NO: 4);
(iii) 5'-catcctggaGGCTAGCTACAACGAgagcaggct (SEQ ID NO: 5);
(iv) 5'-ccgcggccaGGCTAGCTACAACGAcctggacga (SEQ ID NO: 6);
(v) 5'-ccgctgccaGGCTAGCTACAACGAcccggacgt (SEQ ID NO: 7);
(vi) 5'-gcggggacaGGCTAGCTACAACGAcagctgcat (SEQ ID NO: 8);
(vii) 5'-cagcggggaGGCTAGCTACAACGAatcagctgc (SEQ ID NO: 9); and
(viii) 5'-ggtcagagaGGCTAGCTACAACGActgcagcgg (SEQ ID NO: 10).

26. A DNAzyme as claimed in claim 25 wherein the 3'-end nucleotide residue is inverted in the binding domain contiguous with the 3'-end of the catalytic domain.

27. A DNAzyme as claimed in claim 25 which has the sequence:
5'-ccgcggccaGGCTAGCTACAACCAcctggacga (SEQ ID NO: 6).

28. A DNAzyme as claimed in claim 27 wherein the 3'-end nucleotide residue is inverted in the binding domain contiguous with the 3'-end of the catalytic domain.

29. A pharmaceutical composition comprising a DNAzyme according to claim 1 and a pharmaceutically acceptable carrier.

* * * * *

SEQUENCE LISTING

<160> NUMBER OF SEQ ID NOS: 23

<210> SEQ ID NO 1
<211> LENGTH: 3132
<212> TYPE: DNA
<213> ORGANISM: Homo sapiens

<400> SEQUENCE: 1

```
ccgcagaact tggggagccg ccgccgccat ccgccgccgc agccagcttc cgccgccgca      60
ggaccggccc ctgccccagc ctccgcagcc gcggcgcgtc cacgcccgcc cgcgcccagg     120
gcgagtcggg gtcgccgcct gcacgcttct cagtgttccc cgcgccccgc atgtaacccg     180
gccaggcccc cgcaacggtg tccctgcag ctccagcccc gggctgcacc ccccgcccc      240
gacaccagct ctccagcctg ctcgtccagg atggccgcgg ccaaggccga gatgcagctg     300
atgtccccgc tgcagatctc tgacccgttc ggatcctttc ctcactcgcc caccatggac     360
aactacccta agctggagga gatgatgctg ctgagcaacg gggctcccca gttcctcggc     420
gccgccgggg ccccagaggg cagcggcagc aacagcagca gcagcagcag cggggcggt     480
ggaggcggcg ggggcggcag caacagcagc agcagcagca gcaccttcaa ccctcaggcg     540
gacacgggcg agcagcccta cgagcacctg accgcagagt cttttcctga catctctctg     600
aacaacgaga aggtgctggt ggagaccagt taccccagcc aaaccactcg actgccccc      660
atcacctata ctggccgctt ttccctggag cctgcaccca acagtggcaa caccttgtgg     720
cccgagcccc tcttcagctt ggtcagtggc ctagtgagca tgaccaaccc accggcctcc     780
tcgtcctcag caccatctcc agcggcctcc tccgcctccg cctcccagag cccacccctg     840
agctgcgcag tgccatccaa cgacagcagt cccatttact cagcggcacc caccttcccc     900
acgccgaaca ctgacatttt ccctgagcca caaagccagg ccttcccggg ctcggcaggg     960
acagcgctcc agtacccgcc tcctgcctac cctgccgcca agggtggctt ccaggttccc    1020
atgatccccg actacctgtt tccacagcag caggggatc tgggcctggg caccccagac    1080
cagaagccct tccagggcct ggagagccgc acccagcagc cttcgctaac ccctctgtct    1140
actattaagg cctttgccac tcagtcgggc tcccaggacc tgaaggccct caataccagc    1200
taccagtccc agctcatcaa acccagccgc atgcgcaagt atcccaaccg gcccagcaag    1260
acgcccccc acgaacgccc ttacgcttgc ccagtggagt cctgtgatcg ccgcttctcc    1320
cgctccgacg agctcaccg ccacatccgc atccacacag gccagaagcc cttccagtgc    1380
cgcatctgca tgcgcaactt cagccgcagc gaccacctca ccacccacat ccgcacccac    1440
acaggcgaaa agccccttcgc ctgcgacatc tgtggaagaa agtttgccag gagcgatgaa    1500
cgcaagaggc ataccaagat ccacttgcgg cagaaggaca agaaagcaga caaaagtgtt    1560
gtggcctctc cggccacctc ctctctctct tcctacccgt ccccggttgc tacctcttac    1620
ccgtccccgg ttactacctc ttatccatcc ccggccacca cctcatacccc atcccctgtg    1680
```

-continued

```
cccacctcct tctcctctcc cggctcctcg acctacccat cccctgtgca cagtggcttc    1740
ccctccccgt cggtggccac cacgtactcc tctgttcccc ctgctttccc ggcccaggtc    1800
agcagcttcc cttcctcagc tgtcaccaac tccttcagcg cctccacagg gctttcggac    1860
atgacagcaa ccttttctcc caggacaatt gaaatttgct aaagggaaag gggaaagaaa    1920
gggaaaaggg agaaaaagaa acacaagaga cttaaaggac aggaggagga gatggccata    1980
ggagaggagg gttcctctta ggtcagatgg aggttctcag agccaagtcc tccctctcta    2040
ctggagtgga aggtctattg gccaacaatc ctttctgccc acttccccctt ccccaattac    2100 tattcccttt gacttcagct gcctgaaaca gccatgtcca agttcttcac ctctatccaa    2160
agaacttgat ttgcatggat tttggataaa tcatttcagt atcatctcca tcatatgcct    2220
gaccccttgc tcccttcaat gctagaaaat cgagttggca aaatgggatt tgggcccctc    2280
agagccctgc cctgcacccct tgtacagtgt ctgtgccatg gatttcgttt tcttggggt    2340 actcttgatg tgaagataat ttgcatattc tattgtatta tttggagtta ggtcctcact    2400
tgggggaaaa aaaaaaaaaa aagccaagca aaccaatggt gatcctctat tttgtgatga    2460
tgctgtgaca ataagtttga accttttttt ttgaaacagc agtcccagta ttctcagagc    2520
atgtgtcaga gtgttgttcc gttaaccttt ttgtaaatac tgcttgaccg tactctcaca    2580
tgtggcaaaa tatggtttgg tttttctttt ttttttttga aagtgttttt tcttcgtcct    2640
tttggtttaa aaagtttcac gtcttggtgc cttttgtgtg atgccccttg ctgatggctt    2700
gacatgtgca attgtgaggg acatgctcac ctctagcctt aaggggggca gggagtgatg    2760
atttggggga ggctttggga gcaaaataag gaagagggct gagctgagct tcggttctcc    2820
agaatgtaag aaaacaaaat ctaaacaaaa atctgaactc tcaaaagtct attttttaa    2880 ctgaaaatgt aaatttataa atatattcag gagttggaat gttgtagtta cctactgagt    2940
aggcggcgat ttttgtatgt tatgaacatg cagttcatta ttttgtggtt ctattttact    3000
ttgtacttgt gtttgcttaa acaaagtgac tgtttggctt ataaacacat tgaatgcgct    3060
ttattgccca tgggatatgt ggtgtatatc cttccaaaaa attaaaacga aaataaagta    3120
gctgcgattg gg                                                       3132

<210> SEQ ID NO 2
<211> LENGTH: 15
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Catalytic domain of DNAzyme

<400> SEQUENCE: 2
ggctagctac aacga                                                      15

<210> SEQ ID NO 3
<211> LENGTH: 33
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNAzyme

<400> SEQUENCE: 3
caggggacag gctagctaca acgacgttgc ggg                                  33
```

```
<210> SEQ ID NO 4
<211> LENGTH: 33
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNAzyme

<400> SEQUENCE: 4 tgcagggag gctagctaca acgaaccgtt gcg                                    33

<210> SEQ ID NO 5
<211> LENGTH: 33
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNAzyme

<400> SEQUENCE: 5
catcctggag gctagctaca acgagagcag gct                                    33

<210> SEQ ID NO 6
<211> LENGTH: 33
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNAzyme

<400> SEQUENCE: 6
ccgcggccag gctagctaca acgacctgga cga                                    33

<210> SEQ ID NO 7
<211> LENGTH: 33
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNAzyme

<400> SEQUENCE: 7
ccgctgccag gctagctaca acgacccgga cgt                                    33

<210> SEQ ID NO 8
<211> LENGTH: 33
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNAzyme

<400> SEQUENCE: 8
gcggggacag gctagctaca acgacagctg cat                                    33

<210> SEQ ID NO 9
<211> LENGTH: 33
```

```
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNAzyme

<400> SEQUENCE: 9
cagcggggag gctagctaca acgaatcagc tgc                                    33

<210> SEQ ID NO 10
<211> LENGTH: 33
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNAzyme

<400> SEQUENCE: 10
ggtcagagag gctagctaca acgactgcag cgg                                    33

<210> SEQ ID NO 11
<211> LENGTH: 3068
<212> TYPE: DNA
<213> ORGANISM: Mus musculus

<400> SEQUENCE: 11
ggggagccgc cgccgcgatt cgccgccgcc gccagcttcc gccgccgcaa gatcggcccc         60
tgccccagcc tccgcggcag ccctgcgtcc accacgggcc gcggctaccg ccagcctggg        120
ggcccaccta cactccccgc agtgtgcccc tgcaccccgc atgtaacccg gccaaccccc        180
ggcgagtgtg ccctcagtag cttcggcccc gggctgcgcc caccaccccaa catcagttct        240 ccagctcgct ggtccgggat ggcagcggcc aaggccgaga tgcaattgat gtctccgctg        300
cagatctctg acccgttcgg ctcctttcct cactcaccca ccatggacaa ctaccccaaa        360
ctggaggaga tgatgctgct gagcaacggg gctccccagt tcctcggtgc tgccggaacc        420
ccagagggca gcggcggtaa tagcagcagc agcaccagca gcggggggcgg tggtgggggc        480 ggcagcaaca gcggcagcag cgccttcaat cctcaagggg agccgagcga acaaccctat        540
gagcacctga ccacagagtc ctttttctgac atcgctctga ataatgagaa ggcgatggtg        600
gagacgagtt atcccagcca aacgactcgg ttgcctccca tcacctatac tggccgcttc        660
tccctggagc ccgcacccaa cagtggcaac actttgtggc ctgaaccccct tttcagccta        720 gtcagtggcc tcgtgagcat gaccaatcct ccgacctctt catcctcggc gccttctcca        780
gctgcttcat cgtcttcctc tgcctcccag agcccgcccc tgagctgtgc cgtgccgtcc        840
aacgacagca gtcccatcta ctcggctgcg cccaccttt ctactcccaa cactgacatt        900
tttcctgagc cccaaagcca ggcctttcct ggctcggcag gcacagcctt gcagtacccg        960
cctcctgcct accctgccac caaaggtggt ttccaggttc ccatgatccc tgactatctg       1020
tttccacaac aacagggaga cctgagcctg ggcaccccag accagaagcc cttccagggt       1080
ctggagaacc gtaccagca gccttcgctc actccactat ccactattaa agccttcgcc       1140
actcagtcgg gctcccagga cttaaaggct cttaatacca cctaccaatc ccagctcatc       1200
aaacccagcc gcatgcgcaa gtaccccaac cggccagca agacaccccc ccatgaacgc       1260
ccatatgctt gccctgtcga gtcctgcgat cgccgctttt ctcgctcgga tgagcttacc       1320
```

-continued

```
cgccatatcc gcatccacac aggccagaag cccttccagt gtcgaatctg catgcgtaac    1380
ttcagtcgta gtgaccacct taccaccac atccgcaccc acacaggcga gaagccttt      1440 gcctgtgaca tttgtgggag gaagtttgcc aggagtgatg aacgcaagag catacaaaa    1500 atccatttaa gacagaagga caagaaagca gacaaaagtg tggtggcctc cccggctgcc    1560
tcttcactct cttcttaccc atccccagtg gctacctcct acccatcccc tgccaccacc    1620
tcattcccat cccctgtgcc cacttcctac tcctctcctg gctcctccac ctacccatct    1680
cctgcgcaca gtggcttccc gtcgccgtca gtggccacca cctttgcctc cgttccacct    1740 gctttccccca cccaggtcag cagcttcccg tctgcgggcg tcagcagctc cttcagcacc    1800
tcaactggtc tttcagacat gacagcgacc ttttctccca ggacaattga aatttgctaa    1860
agggaataaa agaaagcaaa gggagaggca ggaaagacat aaaagcacag gagggaagag    1920
atggccgcaa gaggggccac ctcttaggtc agatggaaga tctcagagcc aagtccttct    1980
actcacgagt agaaggaccg ttggccaaca gcccttttcac ttaccatccc tgcctccccc    2040
gtcctgttcc ctttgacttc agctgcctga acagccatg tccaagttct tcacctctat    2100
ccaaaggact tgatttgcat ggtattggat aaatcatttc agtatcctct ccatcacatg    2160 cctggcccttt gctcccttca gcgctagacc atcaagttgg cataaagaaa aaaaaatggg    2220 tttgggcccct cagaaccctg ccctgcatct ttgtacagca tctgtgccat ggattttgtt    2280
ttccttgggg tattcttgat gtgaagataa tttgcatact ctattgtatt atttggagtt    2340
aaatcctcac tttgggggag gggggagcaa agccaagcaa accaatgatg atcctctatt    2400
ttgtgatgac tctgctgtga cattaggttt gaagcatttt ttttttcaag cagcagtcct    2460
aggtattaac tggagcatgt gtcagagtgt tgttccgtta attttgtaaa tactggctcg    2520
actgtaactc tcacatgtga caaagtatgg tttgtttggt tgggttttgt ttttgagaat    2580
ttttttgccc gtcccttttgg tttcaaaagt ttcacgtctt ggtgcctttt gtgtgacacg    2640
ccttccgatg gcttgacatg cgcagatgtg agggacacgc tcaccttagc cttaaggggg    2700
taggagtgat gtgttggggg aggcttgaga gcaaaaacga ggaagagggc tgagctgagc    2760
tttcggtctc cagaatgtaa gaagaaaaaa tttaaacaaa aatctgaact ctcaaaagtc    2820
tatttttcta aactgaaaat gtaaatttat acatctattc aggagttgga gtgttgtggt    2880
tacctactga gtaggctgca gttttttgtat gttatgaaca tgaagttcat tatttttgtgg   2940 ttttatttta ctttgtactt gtgtttgctt aaacaaagta acctgtttgg cttataaaca    3000
cattgaatgc gctctattgc ccatgggata tgtggtgtgt atccttcaga aaaattaaaa    3060
ggaaaaat                                                              3068
```

<210> SEQ ID NO 12
<211> LENGTH: 4321
<212> TYPE: DNA
<213> ORGANISM: Rattus rattus

<400> SEQUENCE: 12

```
ccgcggagcc tcagctctac gcgcctggcg ccctccctac gcgggcgtcc ccgactcccg      60
cgcgcgttca ggctccgggt tgggaaccaa ggagggggag ggtgggtgcg ccgacccgga    120
aacaccatat aaggagcagg aaggatcccc cgccggaaca gaccttattt gggcagcgcc    180
ttatatggag tggcccaata tggccctgcc gcttccggct ctgggaggag gggcgaacgg    240
gggttggggc gggggcaagc tggaactcc aggagcctag cccggaggc cactgccgct    300 gttccaatac taggctttcc aggagcctga gcgctcaggg tgccggagcc ggtcgcaggg    360
```

-continued

```
tggaagcgcc caccgctctt ggatgggagg tcttcacgtc actccgggtc ctcccggtcg    420
gtccttccat attagggctt cctgcttccc atatatggcc atgtacgtca cggcggaggc    480
gggcccgtgc tgtttcagac ccttgaaata gaggccgatt cggggagtcg cgagagatcc    540
cagcgcgcag aacttgggga gccgccgccg cgattcgccg ccgccgccag cttccgccgc    600
cgcaagatcg gccctgccc cagcctccgc ggcagccctg cgtccaccac gggccgcggc     660
caccgccagc ctggggccc acctacactc cccgcagtgt gcccctgcac cccgcatgta    720
acccggccaa catccggcga gtgtgccctc agtagcttcg gccccgggct cgcccacca    780 cccaacatca gctctccagc tcgcacgtcc gggatggcag cggccaaggc cgagatgcaa    840
ttgatgtctc cgctgcagat tctgacccg ttcggctcct ttcctcactc acccaccatg     900
gacaactacc ccaaactgga ggagatgatg ctgctgagca acggggctcc ccagttcctc    960
ggtgctgccg aaccccaga gggcagcggc ggcaataaca gcagcagcag cagcagcagc    1020
agcagcgggg gcggtggtgg gggcggcagc aacagcggca gcagcgcttt caatcctcaa    1080
ggggagccga cgaacaacc ctacgagcac ctgaccacag gtaagcggtg gtctgcgccg     1140
aggctgaatc ccccttcgtg actaccctaa cgtccagtcc tttgcagcac ggacctgcat    1200
ctagatctta gggacgggat tgggatttcc ctctattcca cacagctcca gggacttgtg    1260
ttagagggat gtctggggac ccccaaccc tccatccttg cgggtgcgcg gagggcagac     1320
cgtttgtttt ggatggagaa ctcaagttgc gtgggtggct ggagtggggg agggtttgtt    1380
ttgatgagca gggttgcccc ctcccccgcg cgcgttgtcg cgagccttgt ttgcagcttg    1440
ttcccaagga agggctgaaa tctgtcacca gggatgtccc ccgcccagg gtagggcgc      1500 gcattagctg tggccactag ggtgctgcg ggattccctc accccggacg cctgctgcgg     1560
agcgctctca gagctgcagt agaggggat tctctgtttg cgtcagctgt cgaaatggct     1620
ctgccactgg agcaggtcca ggaacattgc aatctgctgc tatcaattat taaccacatc    1680
gagagtcagt ggtagccggg cgacctcttg cctggccgct tcggctctca tcgtccagtg    1740
attgctctcc agtaaccagg cctctctgtt ctctttcctg ccagagtcct tttctgacat    1800
cgctctgaat aacgagaagg cgctggtgga gacaagttat cccagccaaa ctaccccggtt   1860 gcctccatc acctatactg gccgcttctc cctggagcct gcacccaaca gtggcaacac     1920
tttgtggcct gaaccccttt tcagcctagt cagtggcctt gtgagcatga ccaaccctcc    1980
aacctcttca tcctcagcgc cttctccagc tgcttcatcg tcttcctctg cctcccagag    2040
cccacccctg agctgtgccg tgccgtccaa cgacagcagt cccatttact cagctgcacc    2100
cacctttcct actcccaaca ctgacatttt tcctgagccc caaagccagg cctttcctgg    2160
ctctgcaggc acagccttgc agtacccgcc tcctgcctac cctgccacca agggtggttt    2220
ccaggttccc atgatccctg actatctgtt tccacaacaa cagggagacc tgagcctggg    2280
caccccagac cagaagccct tccagggtct ggagaaccgt acccagcagc cttcgctcac    2340
tccactatcc actatcaaag ccttcgccac tcagtcgggc tcccaggact taaaggctct    2400
taataacacc taccagtccc aactcatcaa acccagccgc atgcgcaagt accccaaccg    2460
gcccagcaag acaccccccc atgaacgccc gtatgcttgc cctgttgagt cctgcgatcg    2520
ccgcttttct cgctcggatg agcttacacg ccacatccgc atccatacag gccagaagcc    2580
cttccagtgt cgaatctgca tgcgtaattt cagtcgtagt gaccaccttta ccacccacat    2640 ccgcacccac acaggcgaga agccttttgc ctgtgacatt tgtgggagaa agtttgccag    2700
```

-continued

```
gagtgatgaa cgcaagaggc ataccaaaat ccacttaaga cagaaggaca agaaagcaga    2760
caaaagtgtc gtggcctcct cagctgcctc ttccctctct tcctacccat ccccagtggc    2820
tacctcctac ccatccccg ccaccacctc atttccatcc ccagtgccca cctcttactc     2880
ctctccgggc tcctctacct acccgtctcc tgcacacagt ggcttccat cgccctcggt     2940 ggccaccacc tatgcctccg tcccacctgc tttccctgcc caggtcagca ccttccagtc    3000 tgcagggtc agcaactcct tcagcacctc aacgggtctt tcagacatga cagcaacctt     3060
ttctcctagg acaattgaaa tttgctaaag ggaatgaaag agagcaaagg gaggggagcg    3120
cgagagacaa taaggacag gagggaagaa atggcccgca agaggggctg cctcttaggt     3180
cagatggaag atctcagagc caagtccttc tagtcagtag aaggcccgtt ggccaccagc    3240
cctttcactt agcgtccctg ccctcccag tccggtcct tttgacttca gctgcctgaa      3300
acagccacgt ccaagttctt cacctctatc caaaggactt gatttgcatg gtattggata    3360
aaccatttca gcatcatctc caccacatgc ctggcccttg ctcccttcag cactagaaca    3420
tcaagttggc tgaaaaaaaa aatgggtctg ggccctcaga accctgccct gtatctttgt    3480
acagcatctg tgccatggat tttgttttcc ttggggtatt cttgatgtga agataatttg    3540
catactctat tgtactattt ggagttaaat tctcactttg ggggaggggg agcaaagcca    3600
agcaaaccaa tggtgatcct ctattttgtg atgatcctgc tgtgacatta ggttgaaac    3660 ttttttttt tttttgaagca gcagtcctag gtattaactg gagcatgtgt cagagtgttg    3720
ttccgttaat tttgtaaata ctgctcgact gtaactctca catgtgacaa atacggttt     3780 gtttggttgg gttttttgtt gttttttgaaa aaaaaatttt tttttgccc gtcccttgg    3840 tttcaaaagt ttcacgtctt ggtgcctttg tgtgacacac cttgccgatg gctggacatg    3900
tgcaatcgtg aggggacacg ctcacctcta gccttaaggg ggtaggagtg atgtttcagg    3960
ggaggcttta gagcacgatg aggaagaggg ctgagctgag ctttggttct ccagaatgta    4020
agaagaaaaa tttaaaacaa aaatctgaac tctcaaaagt ctattttttt aactgaaaat    4080
gtagatttat ccatgttcgg gagttggaat gctgcggtta cctactgagt aggcggtgac    4140
ttttgtatgc tatgaacatg aagttcatta ttttgtggtt ttatttact tcgtacttgt    4200 gtttgcttaa acaaagtgac ttgtttggct tataaacaca ttgaatgcgc tttactgccc    4260
atgggatatg tggtgtgtat ccttcagaaa aattaaaagg aaaataaaga aactaactgg    4320
t                                                                    4321
```

<210> SEQ ID NO 13
<211> LENGTH: 19
<212> TYPE: RNA
<213> ORGANISM: Rattus rattus

<400> SEQUENCE: 13
acguccggga uggcagcgg                                                  19

<210> SEQ ID NO 14
<211> LENGTH: 19
<212> TYPE: RNA
<213> ORGANISM: Homo sapiens

<400> SEQUENCE: 14
ucguccagga uggccgcgg                                                  19

<210> SEQ ID NO 15
<211> LENGTH: 34

```
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNAzyme
<220> FEATURE:
<221> NAME/KEY: misc_feature
<222> LOCATION: (33)..(34)
<223> OTHER INFORMATION: 3'-3-linked T

<400> SEQUENCE: 15
caggggacag gctagctaca acgacgttgc gggt                                    34

<210> SEQ ID NO 16
<211> LENGTH: 34
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNAzyme
<220> FEATURE:
<221> NAME/KEY: misc_feature
<222> LOCATION: (33)..(34)
<223> OTHER INFORMATION: 3'-3-linked T

<400> SEQUENCE: 16
tgcaggggag gctagctaca acgaaccgtt gcgt                                    34

<210> SEQ ID NO 17
<211> LENGTH: 34
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNAzyme
<220> FEATURE:
<221> NAME/KEY: misc_feature
<222> LOCATION: (33)..(34)
<223> OTHER INFORMATION: 3'-3-linked T

<400> SEQUENCE: 17
catcctggag gctagctaca acgagagcag gctt                                    34

<210> SEQ ID NO 18
<211> LENGTH: 34
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNAzyme
<220> FEATURE:
<221> NAME/KEY: misc_feature
<222> LOCATION: (33)..(34)
<223> OTHER INFORMATION: 3'-3-linked T

<400> SEQUENCE: 18
tcagctgcag gctagctaca acgactcggc cttt                                    34

<210> SEQ ID NO 19
<211> LENGTH: 34
<212> TYPE: DNA
<213> ORGANISM: Artificial
<220> FEATURE:
```

-continued

```
<223> OTHER INFORMATION: synthetic
<220> FEATURE:
<221> NAME/KEY: misc_feature
<223> OTHER INFORMATION: DNAzyme
<220> FEATURE:
<221> NAME/KEY: misc_feature
<222> LOCATION: (33)..(34)
<223> OTHER INFORMATION: 3'-3-linked T

<400> SEQUENCE: 19
gcggggacag gctagctaca acgacagctg catt                                    34

<210> SEQ ID NO 20
<211> LENGTH: 15
<212> TYPE: DNA
<213> ORGANISM: Rattus rattus

<400> SEQUENCE: 20
cttggccgct gccat                                                         15

<210> SEQ ID NO 21
<211> LENGTH: 22
<212> TYPE: RNA
<213> ORGANISM: Synthetic Rat

<400> SEQUENCE: 21
gcacguccgg auggcagcgg cc                                                 22

<210> SEQ ID NO 22
<211> LENGTH: 34
<212> TYPE: DNA
<213> ORGANISM: Synthetic Rat

<400> SEQUENCE: 22
ccgctgccag gctagctaca acgacccgga cgtt                                    34

<210> SEQ ID NO 23
<211> LENGTH: 34
<212> TYPE: DNA
<213> ORGANISM: Synthetic Rat

<400> SEQUENCE: 23
gccagccgcg gctagctaca acgatggctc cact                                    34
```